United States Patent
Froehlich et al.

(10) Patent No.: US 9,598,450 B2
(45) Date of Patent: Mar. 21, 2017

(54) EMISSIVE COMPOUNDS FOR ORGANIC LIGHT-EMITTING DIODES

(75) Inventors: Jesse Dan Froehlich, Vista, CA (US); Rebecca Romero, Escondido, CA (US); Amane Mochizuki, Carlsbad, CA (US); Sheng Li, Vista, CA (US); Nobukazu Negishi, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 1234 days.

(21) Appl. No.: 13/521,022

(22) PCT Filed: Dec. 29, 2010

(86) PCT No.: PCT/US2010/062439
§ 371 (c)(1),
(2), (4) Date: Dec. 18, 2012

(87) PCT Pub. No.: WO2011/149500
PCT Pub. Date: Dec. 1, 2011

(65) Prior Publication Data
US 2013/0087772 A1   Apr. 11, 2013

Related U.S. Application Data

(60) Provisional application No. 61/293,152, filed on Jan. 7, 2010.

(51) Int. Cl.
| | | |
|---|---|---|
| H01L 51/54 | (2006.01) | |
| C09K 11/06 | (2006.01) | |
| C07F 15/00 | (2006.01) | |
| H01L 51/00 | (2006.01) | |
| H01L 51/50 | (2006.01) | |

(52) U.S. Cl.
CPC .......... *C07F 15/0086* (2013.01); *C09K 11/06* (2013.01); *H01L 51/0087* (2013.01); *H01L 51/50* (2013.01); *C09K 2211/1029* (2013.01); *C09K 2211/1048* (2013.01); *C09K 2211/185* (2013.01); *H01L 51/0037* (2013.01); *H01L 51/5016* (2013.01)

(58) Field of Classification Search
CPC .. C07F 15/0086; H01L 51/0087; H01L 51/50; H01L 51/5016; C09K 11/06; C09K 2211/1029; C09K 2211/1044; C09K 2211/1048; C09K 2211/185
See application file for complete search history.

(56) References Cited

U.S. PATENT DOCUMENTS

| | | |
|---|---|---|
| 6,517,958 B1 | 2/2003 | Sellinger et al. |
| 6,869,695 B2 | 3/2005 | Thompson et al. |
| 7,250,226 B2 | 7/2007 | Tokito et al. |
| 2005/0017629 A1 | 1/2005 | Vitukhnovsky et al. |
| 2005/0260445 A1 | 11/2005 | Walters et al. |
| 2006/0063026 A1 | 3/2006 | Holmes et al. |
| 2006/0102890 A1 | 5/2006 | Yamahara et al. |

FOREIGN PATENT DOCUMENTS

| | | |
|---|---|---|
| CN | 101 125 913 | 2/2008 |
| EP | 1 191 613 | 3/2002 |
| EP | 1 932 851 | 6/2008 |
| JP | 2005-314663 | 11/2005 |
| JP | 2007-277170 | 10/2007 |
| WO | WO 03/040257 | 5/2003 |
| WO | WO 2005/083033 | 9/2005 |
| WO | WO 2005/097942 | 10/2005 |
| WO | WO 2005/101912 | 10/2005 |
| WO | WO 2010/090925 | 8/2010 |
| WO | WO 2011/149500 | 12/2011 |

OTHER PUBLICATIONS

English language machine translation of CN 101125913 A, 2007.*
English language machine translation of WO 2005/101912 A1, 2005.*
Cho et al. "Phosphorescent, green-emitting Ir(III) complexes with carbazolyl-substituted 2-phenylpyridine ligands: effects of binding mode of the carbazole group on photoluminescence and electrophosphorescence." Dyes and Pigments. vol. 83, pp. 218-224. 2009.*
Adamovich et al., "High Efficiency Single Dopant White Electrophosphorescent Light Emitting Diodes", New Journal of Chemistry, 2002, vol. 26, pp. 1171-1178.
Baldo et al., "High-Efficiency Phosphorescent Emission from Organic Electroluminescent Devices", Nature, Sep. 10, 1998, vol. 395, pp. 151-154.
Brooks et al., "Synthesis and Characterization of Phosphorescent Cyclometalated Platinum Complexes", Inorganic Chemistry, 2002, vol. 41, pp. 3055-3066.
Cheng et al., "White Organic Light-Emitting Devices with a Phosphorescent Multiple Emissive Layer", Applied Physics Letters, vol. 89, 2006, pp. 045304-1-045304-3.
D'Andrade et al., "Efficient Organic Electrophosphorescent White-Light-Emitting Device With a Triple Doped Emissive Layer", Advanced Materials, Apr. 5, 2004, vol. 16, Issue 7, pp. 624-628.
Furuta et al., "Platinum-Functionalized Random Copolymers for Use in Solution-Processible, Efficient, Near-White Organic Light-Emitting Diodes", Journal of American Chemical Society, Dec. 1, 2004, vol. 126, No. 47, 15388-15389.
Gustafsson et al. "Flexible Light-Emitting Diodes Made from Soluble Conducting Polymer," Nature, Jun. 11, 1992, vol. 357, pp. 477-479.
He et al., "Phosphorescent Platinum(II) Complexes Derived from Multifunctional Chromophores: Synthesis, Structures, Photophysics, and Electroluminescence," Inorganic Chemistry, Aug. 18, 2006, vol. 45, pp. 10922-10937.

(Continued)

*Primary Examiner* — Marie R. Yamnitzky
(74) *Attorney, Agent, or Firm* — Knobbe, Martens, Olson & Bear, LLP

(57) ABSTRACT

Disclosed herein are compounds containing an optionally substituted (2-phenylpyridinato-N,C$^{2'}$)(2,4-pentanedionato) Pt(II). Some embodiments provide a light-emitting device, having an anode layer, a cathode layer, and a light-emitting layer positioned between, and electrically connected to, the anode layer and the cathode layer, wherein the light-emitting layer contains a compound disclosed herein.

17 Claims, 4 Drawing Sheets

(56) References Cited

OTHER PUBLICATIONS

Ho et al., "Synthesis, Characterization, Photophysics and Electrophosphorescent Applications of Phosphorescent Platinum Cyclometalated Complexes with 9-Arylcarbazole Moieties," Journal of Organometallic Chemistry, 2008, vol. 694, pp. 2735-2749.
Kido et al., "Multilayer White Light-Emitting Organic Electroluminescent Device", Science, Mar. 3, 1995, vol. 267, pp. 1332-1334.
Kido et al., "White Light-Emitting Organic Electroluminescent Devices Using the Poly(N-Vinylcarbazole) Emitter Layer Doped with Three Fluorescent Chromophores", Applied Physics Letters, Feb. 1994, vol. 64, Issue 815.
Liu et al., "Green and Blue-Green Phosphorescent Heteroleptic Iridium Complexes Containing Carbazole-Functionalized β-diketonate for Non-Doped Organic Light-Emitting Diodes," Organic Electronics, 2008, vol. 9, pp. 171-182.
Tsuzuki et al., "Organic Light-Emitting Diodes Using Multifunctional Phoshorescent Dendrimers with Iridium-Complex Core and Charge-Transporting Dendrons," Japanese Journal of Applied Physics, 2005, vol. 44, No. 6A, pp. 4151-4154.
Williams et al., "Excimer-Based White Phosphorescent Organic Light Emitting Diodes with Nearly 100% Internal Quantum Efficiency", Advanced Materials, 2007, vol. 19, pp. 197-202.
Yin et al., "Synthesis, Structure, and Photophysical Properties of Luminescent Platinum(II) Complexes Containing Cyclometalated 4-Styryl-Functionalized 2-Phenylpyridine Ligands," Inorganic Chemistry, 2006, vol. 45, No. 21, pp. 8584-8596.
Zhou et al., "A Versatile Color Tuning Stategy for Iridium(III) and Platinum(II) Electrophosphors by Shifting the Charge-Transfer States with an Electron-Deficient Core," Journal of Materials Chemistry, 2009, vol. 19, pp. 1872-1883.
Zhou et al., "Multifunctional Metallophosphors with Anti-Triplet-Triplet Annihilation Properties for Solution-Processable Electroluminescent Devices," Journal of Materials Chemistry, 2008, vol. 18, pp. 1799-1809.
Zhou et al., "New Platinum(II) Complexes as Triplet Emitters for High-Efficiency Monochromatic Pure Orange Electroluminescent Devices," Journal of Organo Metallic Chemistry, 2007, vol. 692, pp. 3461-3473.
International Search Report and the Written Opinion in PCT Application No. PCT/US2010/062439, dated May 10, 2011.

* cited by examiner

EMISSIVE COMPOUNDS FOR ORGANIC LIGHT-EMITTING DIODES

CROSS-REFERENCE TO RELATED APPLICATION

This application is the U.S. National Phase under 35 U.S.C. §371 of International Application No. PCT/US2010/062439, filed Dec. 29, 2010 (published as WO 2011/149500 and herein incorporated by reference), which claims the benefit of U.S. Provisional Application No. 61/293,152, filed Jan. 7, 2010, which is incorporated by reference herein in its entirety.

BACKGROUND OF THE INVENTION

Field of the Invention

This invention relates to emissive compounds such as those useful in light emitting diodes or devices.

Description of the Related Art

Organic electroluminescent devices capable of emitting white light are desirable because of their potential utility as backplane lights for LCD displays, overhead lighting and other lightweight, low profile, low power lighting applications. White light-emitting Organic Light-Emitting Diode (OLED) devices with high color purity and brightness exceeding 2000 cd/m have been demonstrated by utilizing several fluorescent dyes either doped into one emission layer or segregated into several emission layers. Recently, phosphorescent dyes have been used more frequently as the source of emission in OLEDs because of their 100% maximum theoretical efficiency as compared the theoretical 25% maximum efficiency of fluorescent dyes which emit only from the singlet state. White light emission has been achieved from phosphorescent OLEDs by a number of techniques such as co-doping red, green, and blue phosphors into a single emission layer, and building up a multilayer device with each layer containing a different color phosphor.

A single emissive layer may be desired for ease of device fabrication. However, when multiple dopants are present in the same layer, energy transfer from the high energy dopants to the low energy dopants may be a problem. This may make color balance difficult because the energy transfer may cause more frequent emission from the low energy dopant than from the high energy dopant. In other words, the higher energy dopant may transfer its energy to the low energy dopant instead of emitting the energy as light in the blue range of the visible spectrum. In turn, a greater number of lower energy dopants may emit more energy as light in the red range of the visible spectrum because a greater number of lower energy dopants may be in an excited state due to the energy transfer from the higher energy dopants. Segregation of the various emitters into separate layers may help to overcome the energy transfer problem. However a multilayered device may be more difficult to fabricate and minor changes in layer thickness may result in a significant change in color balance.

One approach to addressing these difficulties has been to prepare a single dopant that can emit white light by the combination of blue emission in its monomer state and orange-red emission from aggregate or excimer species. An excimer is an emissive excited state whose wave function overlaps two adjacent molecules of like composition. One phosphor capable of excimer formation is platinum(II) (2-(4',6'-difluorophenyl)pyridinato-N,C$^{2'}$) (2,4-pentanedionato-O,O)$^6$ (FPt). The ratio of monomer/excimer emission is highly concentration dependant with higher concentrations leading to more excimer emission. By careful control of the concentration of FPt, monomer and excimer emission may be balanced and white light may be produced.

On potential problem with FPt is that it may suffer from phase separation or aggregation from electron-transport materials, hole-transport materials, or other host materials which are often helpful to use in an emissive layer of an LED. This may disturb the careful control of the FPt concentration which may be needed to achieve the desired color balance. Thus, there is a continuing need for single-molecule white light emitting phosphors.

SUMMARY OF THE INVENTION

Some embodiments provide a compound represented by Formula I:

wherein a is 1, 2, 3, or 4; A is optionally substituted (2-phenylpyridinato-N,C$^{2'}$)(2,4-pentanedionato)Pt(II); each D is independently a moiety consisting of: from about 0 to about 5 repeat units, wherein each repeat unit is independently represented by one of Formulas II-IV:

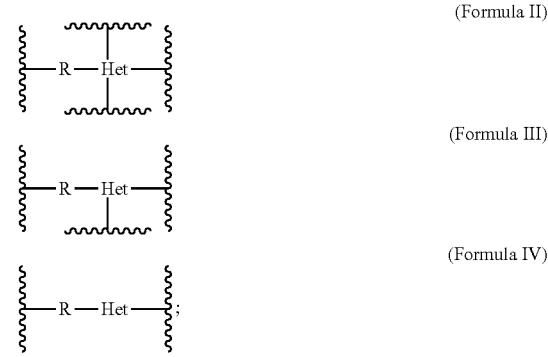

and from about 1 to about 11 terminal units independently represented by Formula V:

wherein each R is independently C$_{1-8}$ alkyl; and each Het is independently an optionally substituted C$_{8-30}$ polycyclic heteroaromatic ring system.

Some embodiments provide a light-emitting device, comprising: an anode layer; a cathode layer; and a light-emitting layer positioned between, and electrically connected to, the anode layer and the cathode layer, the light-emitting layer comprising a compound disclosed herein.

These and other embodiments are described in greater detail below.

DETAILED DESCRIPTION OF THE PREFERRED EMBODIMENT

Figure 1:
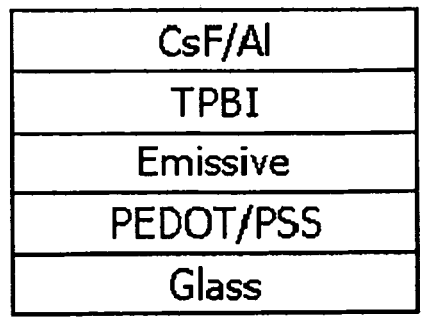
FIG. 1 shows an exemplary configuration of an organic light-emitting device comprising a compound of Formula 1.

Unless unambiguously indicated otherwise, a name or a formula representing a chemical genus or species is intended to include any stereoisomers related to the name or formula, such as enantiomers and diastereomers, including both a pure form of any isomer or a mixture of isomers.

Unless otherwise indicated, when a structural feature such as alkyl or aryl is referred to as being "optionally substituted," it indicates that the feature may have no substituents or may have one or more substituents. A feature that is "substituted" has one or more substituents. The term "substituent" has the ordinary meaning known to one of ordinary skill in the art. In some embodiments, the substituent is a halogen, OH, SH, NO$_2$, a C$_{1-20}$ hydrocarbon, or a C$_{1-20}$ heterohydrocarbon moiety, meaning a hydrocarbon moiety having from 1-10 heteroatom replacements, wherein the heteroatom replacements are selected from: 1) replacing a C with N$^+$ (e.g. CH$_2$NH$_3$$^+$ instead of CH$_2$CH$_3$), 2) replacing a CH with N (e.g. —NHCH$_3$ instead of —CH$_2$CH$_3$ or C═NH instead of C═CH$_2$), 3) replacing a CH$_2$ with O, S, or SO$_2$ (e.g. CH$_2$OCH$_3$ instead of CH$_2$CH$_2$CH$_3$ or C═O instead of C═CH$_2$, or 4) replacing H with a halogen or —NO$_2$ (e.g. CH$_2$F instead of CH$_3$). In some embodiments, the substituent comprises at least one carbon atom or heteroatom, and the substituent has from 0-20 carbon atoms or from 0-10 carbon atoms, and from 0-10 heteroatoms, or from 0-5 heteroatoms, wherein each heteroatom is independently selected from: N, O, S, F, Cl, Br, and I. In some embodiments, Examples include, but are not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxyl, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, —CNO, —NCO, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

The term "(2-phenylpyridinato-N,C$^{2'}$)(2,4-pentanedionato)Pt(II)" as used herein refers to the ring system:

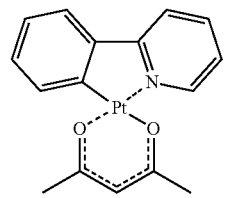

If the (2-phenylpyridinato-N,C$^{2'}$)(2,4-pentanedionato)Pt(II) is substituted, the substituents attach to a carbon atom which would otherwise bear a hydrogen.

The term "alkyl" as used herein refers to a hydrocarbon moiety containing no double or triple bonds. Alkyl may be linear, branched, cyclic, or a combination thereof. Examples of alkyl groups include but are not limited to methyl, ethyl, propyl isomers, cyclopropyl isomers, butyl isomers, cyclobutyl isomers, etc. A designation such as "C$_{1-30}$ alkyl" refers to the number of carbon atoms the alkyl may have, e.g. "C$_{1-30}$ alkyl" may have from 1-30 carbon atoms. The term alkyl includes terminal alkyl groups, e.g., of the general formula —C$_n$H$_{2n+1}$, as well as linking alkyl groups, e.g., of the general formula —C$_n$H$_{2n}$—.

The term "aryl" as used herein refers to an aromatic ring or ring system. Exemplary non-limiting aryl groups are phenyl, naphthyl, etc. In some embodiments, the aryl is carbocyclic, meaning that all of the atoms of the aromatic ring(s) of the ring system are carbon. The designation "C$_{6-10}$ aryl" refers to the fact that there are 6-10 carbon atoms in the aromatic ring or ring system, but does not limit the number of carbon atoms in any substituents.

The term "heteroaryl" as used herein refers to an aromatic ring or ring system having one or more atoms in an aromatic ring selected from nitrogen, oxygen, or sulfur. Examples include furyl, thienyl, oxazolyl, imidazolyl, pyridinyl, pyridazinyl, triazinyl, pyridinyl, pyrimidinyl, pyrazinyl, benzoimidazolyl, indolyl, benzooxazolyl, etc. The designation "C$_{3-10}$ heteroaryl" refers to the fact that there are 3-10 carbon atoms in the aromatic ring or ring system, but does not limit the number of carbon atoms in any substituents.

The term "polycyclic heteroaromatic ring system" as used herein refers to an aromatic ring system comprising at least one heteroatom in at least one ring. The rings of the ring system may be fused such as in:

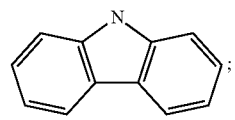 [SMILES: c1ccc2c(c1)[nH]c1ccccc12]

or may be connected by at least one single covalent bond, such as in

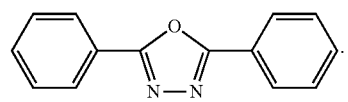 [SMILES: c1ccc(-c2nnc(-c3ccccc3)o2)cc1]

The designation "C$_{8-30}$ polycyclic heteroaromatic ring system" refers to the fact that there are 8-30 carbon atoms in the polycyclic heteroaromatic ring system, but does not limit the number of carbon atoms in any substituents.

The term "alkoxy" as used herein refers to an —O-alkyl moiety, such as —O-methyl, —O-ethyl, —O—$C_3H_7$, —O—$C_4H_9$, —O—$C_5H_{11}$, —O—$C_6H_{13}$, etc.

The term "halo" as used herein refers to a halogen such as F, Cl, Br, or I.

The term "haloalkyl" as used herein refers to alkyl having at least one halogen in a position normally occupied by hydrogen in an alkyl moiety. Examples include, but are not limited to chloroalkyl such as chloromethyl, chloroethyl, etc; fluoroalkyl such as fluoromethyl, fluoroethyl, etc.; perfluoroalkyl, meaning alkyl having all hydrogens replaced with fluorine such as $CF_3$, $CF_2CF_3$, $C_3F_7$, $C_4F_9$, $C_5F_{11}$, etc; and the like.

The term "work function" has the ordinary meaning known to one of ordinary skill in the art. In some embodiments, a "work function" of a metal is a measure of the minimum energy required to extract an electron from the surface of the metal.

The term "high work function metal" has the ordinary meaning known to one of ordinary skill in the art. In some embodiments, a "high work function" metal is a metal or alloy that easily injects holes and typically has a work function greater than or equal to about 4.5.

The term "low work function metal" has the ordinary meaning known to one of ordinary skill in the art. In some embodiments, a "low work function metal" is a metal or alloy that easily loses electrons and typically has a work function less than about 4.3.

The term "white light emitting material" has the ordinary meaning known to one of ordinary skill in the art. In some embodiments, a material is white light-emitting if it emits white light. White light may be light having the approximate CIE color coordinates (X=1/3, Y=1/3). The CIE color coordinates (X=1/3, Y=1/3) may be defined as the achromatic point. The X and Y color coordinates are weights applied to the CIE primaries to match a color. A more detailed description of these terms may be found in CIE 1971, International Commission on Illumination, Colorimetry: Official Recommendations of the International Commission on Illumination, Publication CIE No. (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

With respect to Formula I, a is 1, 2, 3, or 4, Formulas Ia-Id illustrate examples of different values for a.

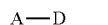  Formula Ia

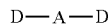  Formula Ib

  Formula Ic

  Formula Id

The D moieties directly attach to a carbon atom of the optionally substituted (2-phenylpyridinato-N,$C^{2'}$)(2,4-pentanedionato)Pt(II).

With respect to Formula I, or Formulas Ia-Id, each D is independently a moiety consisting of: from about 0 to about 5, (e.g., 0, 1, 2, 3, 4, or 5) repeat units; and from about 1 to about 11, (e.g., 0, 1, 2, 3, 4, 5, 6, 7, 8, 9, 10, or 11) terminal units, as defined above.

With respect to Formulas II-V, attachment points to the remainder of the molecule are indicated by:

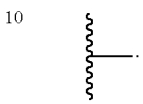

In some embodiments, the R group may directly attach to A. For the remaining attachment points, e.g. in Formulas II-IV, a terminal unit represented by Formula IV may directly attach.

In some embodiments related to Formulas II-IV, Het may directly attach to A. For the remaining attachment points, a terminal unit represented by Formula IV may directly attach.

Thus, for example, in some embodiments, D may be a combination of 1 repeat unit of Formula III and 2 terminal units of Formula V represented as follows:

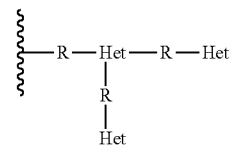

Thus, in some embodiments, D may be:

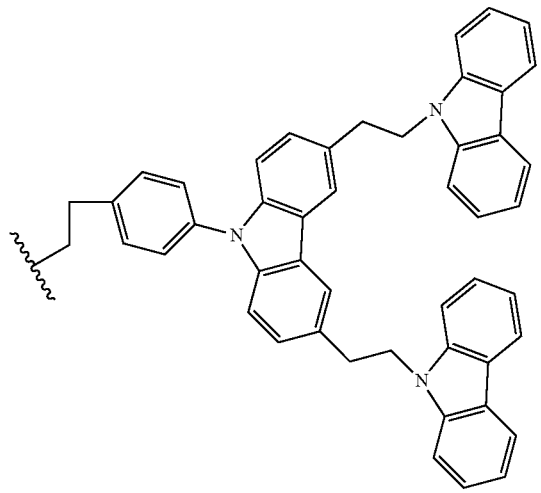 [SMILES: *CCc1ccc(-n2c3ccc(CCn4c5ccccc5c5ccccc54)cc3c3cc(CCn4c5ccccc5c5ccccc54)ccc32)cc1]

With respect to Formulas II-V, each R is independently $C_{1-8}$ alkyl, including, but not limited to: cycloalkyl such as cyclopropyl, cyclobutyl, cyclopentyl, cyclohexyl, etc.; branched alkyl; and linear alkyl such as —$(CH_2)$—, —$(CH_2)_2$—, —$(CH_2)_3$—, —$(CH_2)_4$—, —$(CH_2)_5$—, —$(CH_2)_6$—, etc. In some embodiments, each R is independently $C_{2-4}$ alkyl, such as —$C_2H_4$—, —$C_3H_6$—, cyclopropyl, cyclobutyl, etc. In some embodiments, at least one R is —$(CH_2)_2$—, or alternatively, each R is —$(CH_2)_2$—.

With respect to Formulas II-V, each Het is an optionally substituted $C_{8-30}$ polycyclic heteroaromatic ring system. In some embodiments, at least one Het is one of the following substituted polycyclic heteroaromatic ring systems with 0, 1, 2, 3, or 4 substituents independently selected from halo, $C_{1-6}$ alkyl, and $C_{1-6}$ alkoxy:

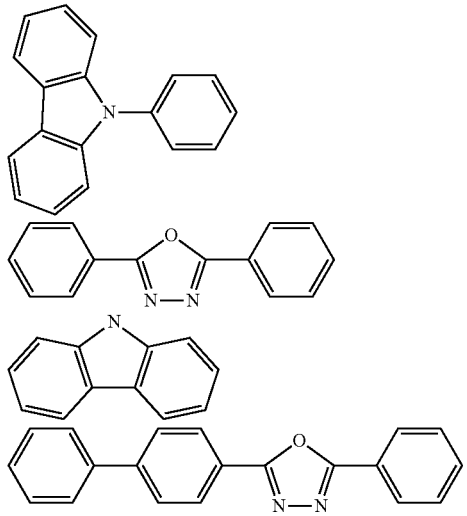

In some embodiments, D is selected from:

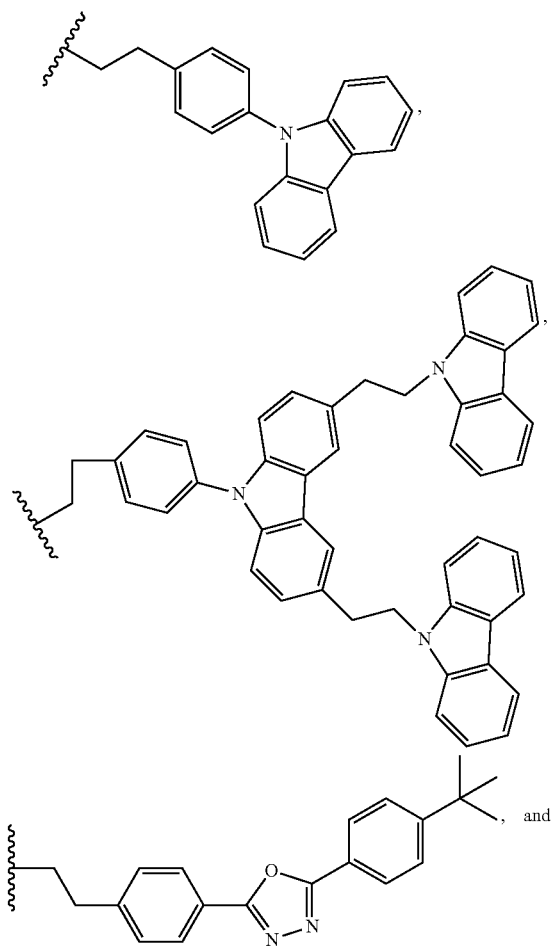

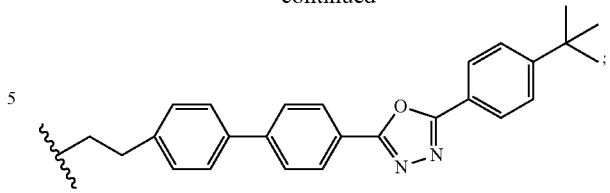

wherein all aromatic rings are optionally substituted.

Some embodiments provide a compound further represented by Formula VI:

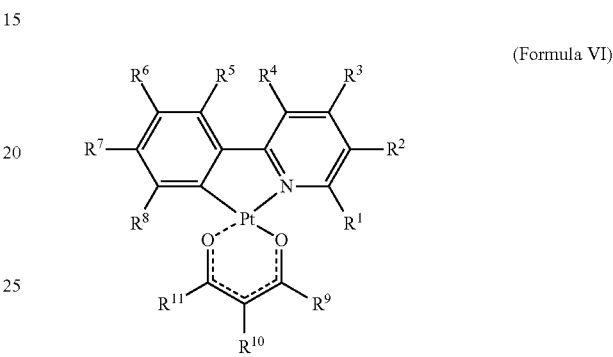

(Formula VI)

With respect to Formula VI, $R^1$, $R^3$, $R^4$, $R^5$, $R^6$, $R^7$, and $R^8$ are independently hydrogen; $C_{1-30}$ alkyl, such as methyl, ethyl, propyl isomers, butyl isomers, pentyl isomers, hexyl isomers, cyclopropyl isomers, cyclobutyl isomers, cyclopentyl isomers, cyclohexyl isomers, etc; $C_{1-30}$ alkoxy, such as methoxy, ethoxy, propyloxy isomers, butyloxy isomers, pentyloxy isomers, hexyloxy, cyclopropyloxy isomers, cyclobutyloxy isomers, cyclopentyloxy isomers, cyclohexyloxy isomers, etc.; halo, such as F, Cl, Br, I, etc.; $C_{1-6}$ haloalkyl, including perfluoroalkyl such as $CF_3$, $CF_2CF_3$, etc.; optionally substituted $C_{6-10}$ aryl; or optionally substituted $C_{3-10}$ heteroaryl. In some embodiments, $R^3$ is $C_{1-6}$ alkyl, $C_{1-6}$ alkoxy, or alternatively, methoxy. In some embodiments, at least one of $R^5$, $R^6$, $R^7$, and $R^8$ is halo or $C_{1-6}$ haloalkyl. In some embodiments, $R^5$ and $R^7$ are F. In some embodiments, $R^6$ and $R^8$ are $CF_3$.

With respect to Formula VI, at least one of $R^2$, $R^9$, $R^{10}$ and $R^{11}$ is independently D as described above for Formula I and Formulas Ia-Id. If not all of $R^2$, $R^9$, $R^{10}$ and $R^{11}$ are D, then any of $R^2$, $R^9$, $R^{10}$ and $R^{11}$ which are not D, are independently hydrogen; $C_{1-30}$ alkyl, such as methyl, ethyl, propyl isomers, butyl isomers, pentyl isomers, hexyl isomers, cyclopropyl isomers, cyclobutyl isomers, cyclopentyl isomers, cyclohexyl isomers, etc; $C_{1-30}$ alkoxy, such as methoxy, ethoxy, propyloxy isomers, butyloxy isomers, pentyloxy isomers, hexyloxy isomers, cyclopropyloxy isomers, cyclobutyloxy isomers, cyclopentyloxy isomers, cyclohexyloxy isomers, etc.; halo, such as F, Cl, Br, I, etc.; $C_{1-6}$ haloalkyl, including perfluoroalkyl such as $CF_3$, $CF_2CF_3$, etc.; optionally substituted $C_{6-10}$ aryl; or optionally substituted $C_{3-10}$ heteroaryl.

In some embodiments, at least one of $R^2$, $R^9$, $R^{10}$ and $R^{11}$ is independently selected from:

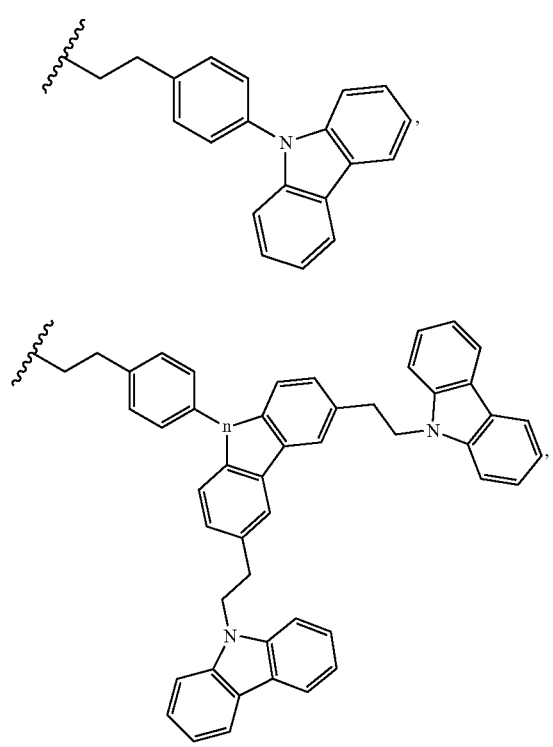

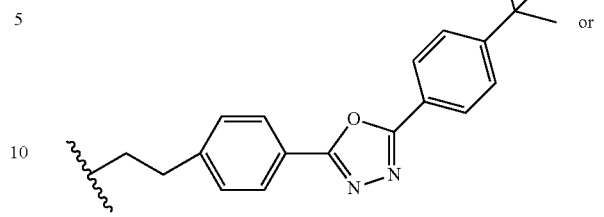

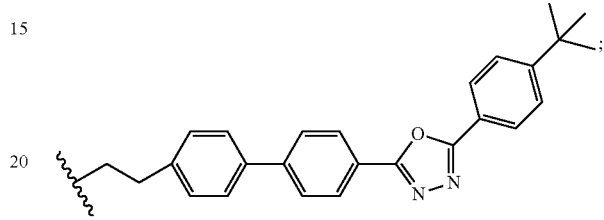

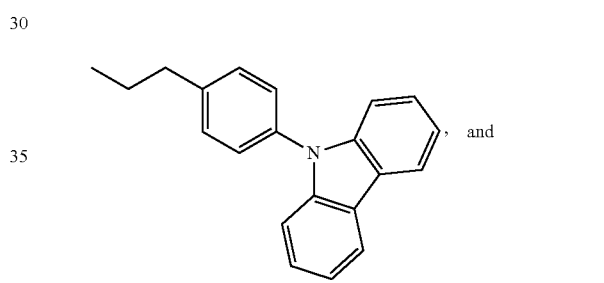

$R^3$ is selected from hydrogen or methoxy; $R^5$ and $R^7$ are hydrogen, methyl, t-butyl $CF_3$ or F; $R^6$ and $R^8$ are hydrogen or $CF_3$; and at least one of $R^9$, $R^{10}$ and $R^{11}$ are selected from

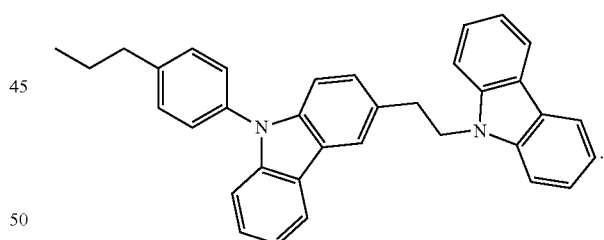

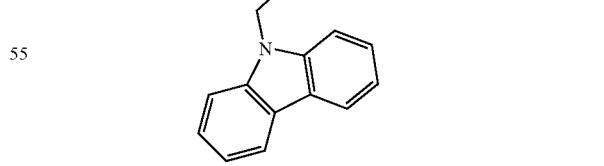

In some embodiments related to Formula VI, $R^1$, $R^4$, $R^6$ and $R^8$ are hydrogen; $R^2$ is

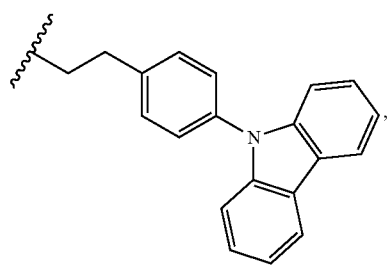

In some embodiments, at least one of $R^1$, $R^2$, $R^3$, $R^4$, $R^5$, $R^7$, $R^7$, $R^8$, $R^9$, $R^{10}$, and $R^{11}$ is $C_{1-6}$ alkyl, such as methyl, ethyl, a propyl isomer, a butyl isomer, a pentyl isomer, or a hexyl isomer. For example, $R^{11}$ may be methyl or t-butyl in some embodiments.

Some embodiments comprise a compound selected from:
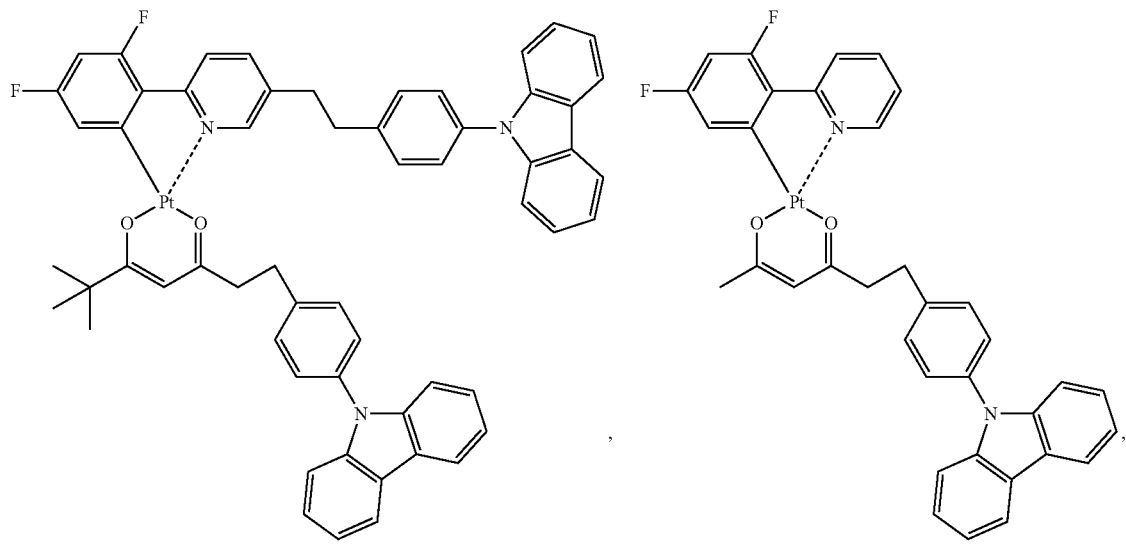
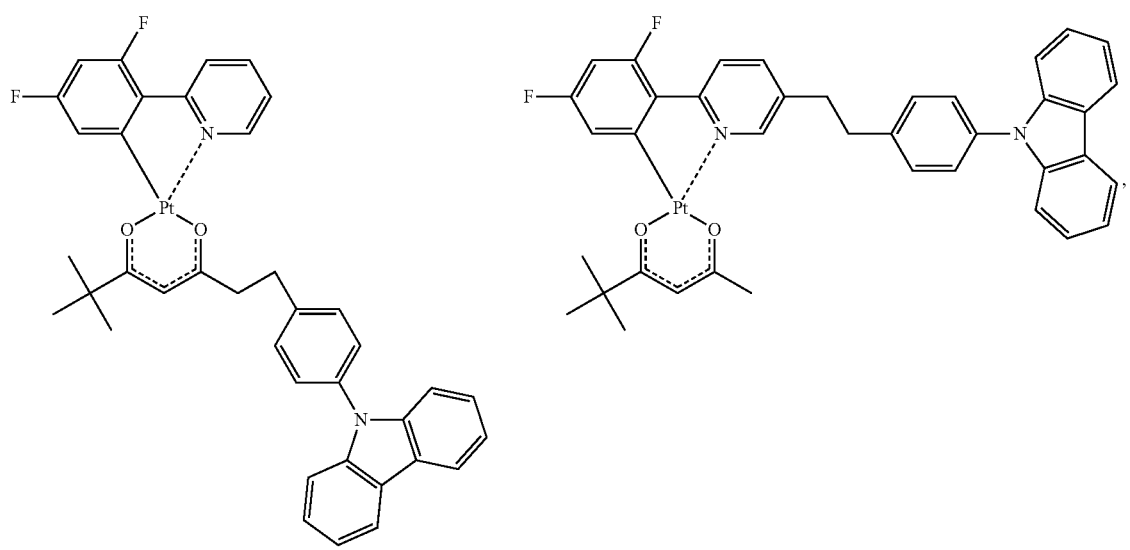
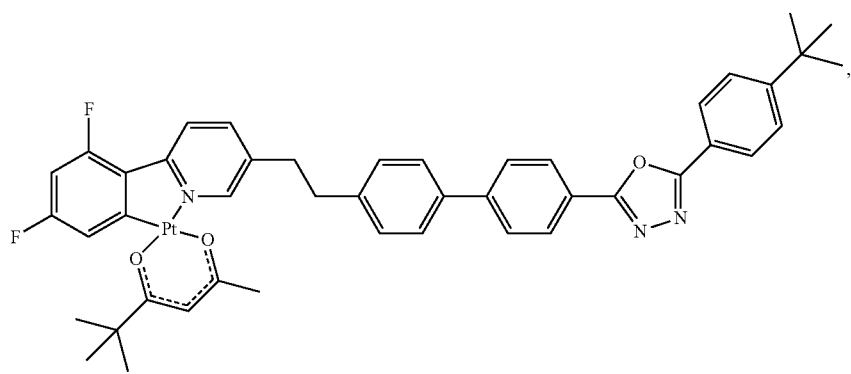

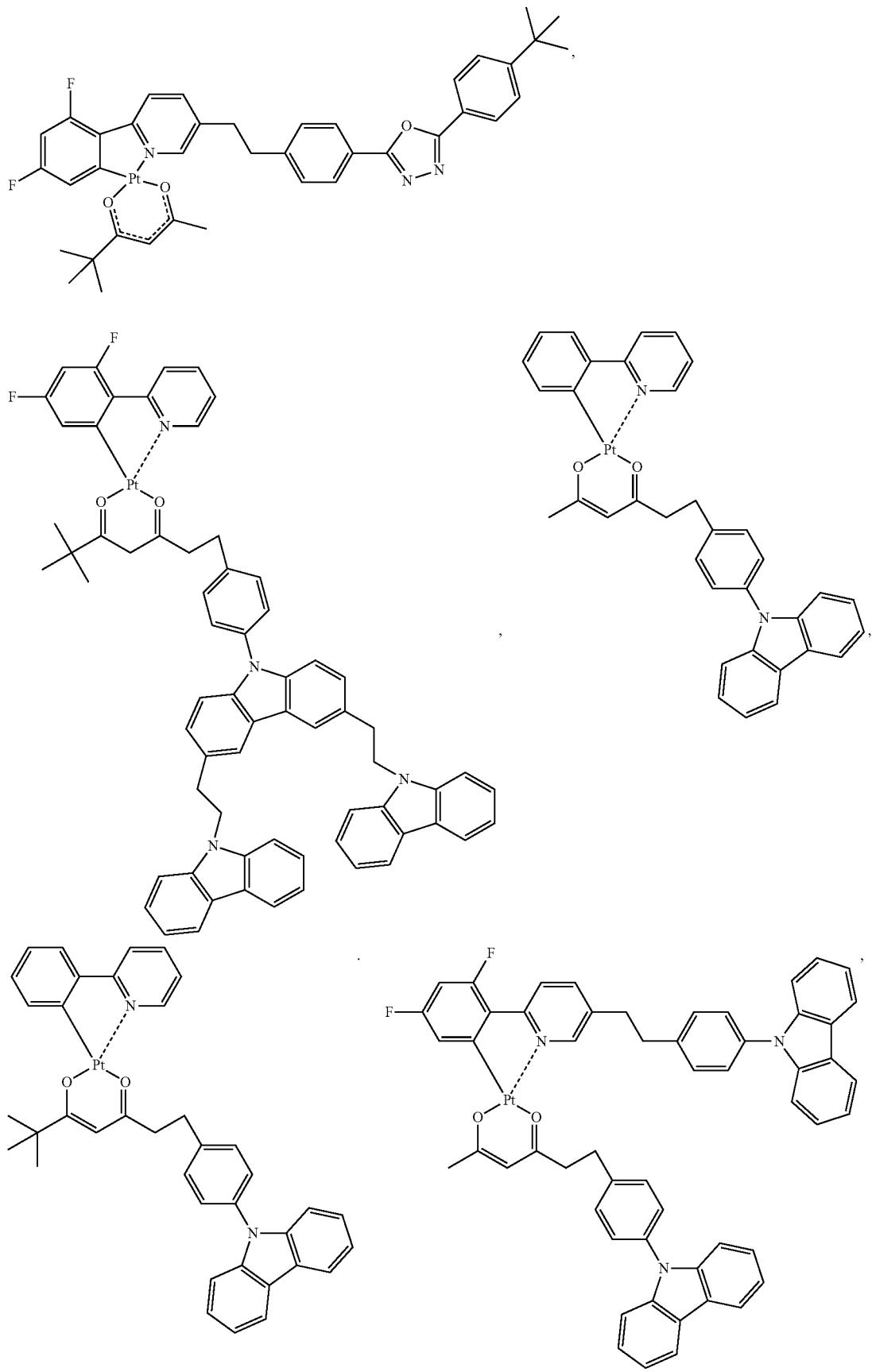

-continued
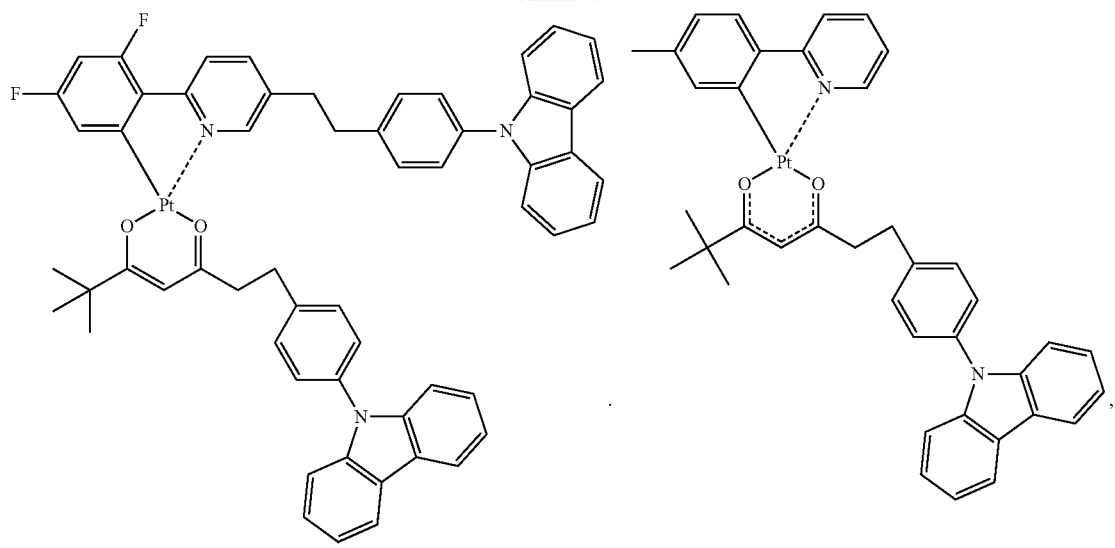
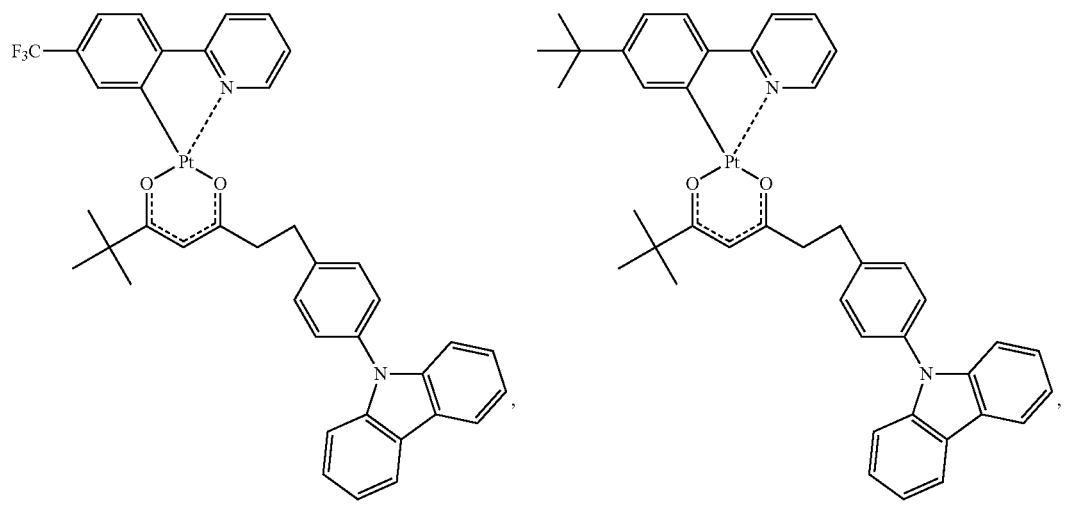
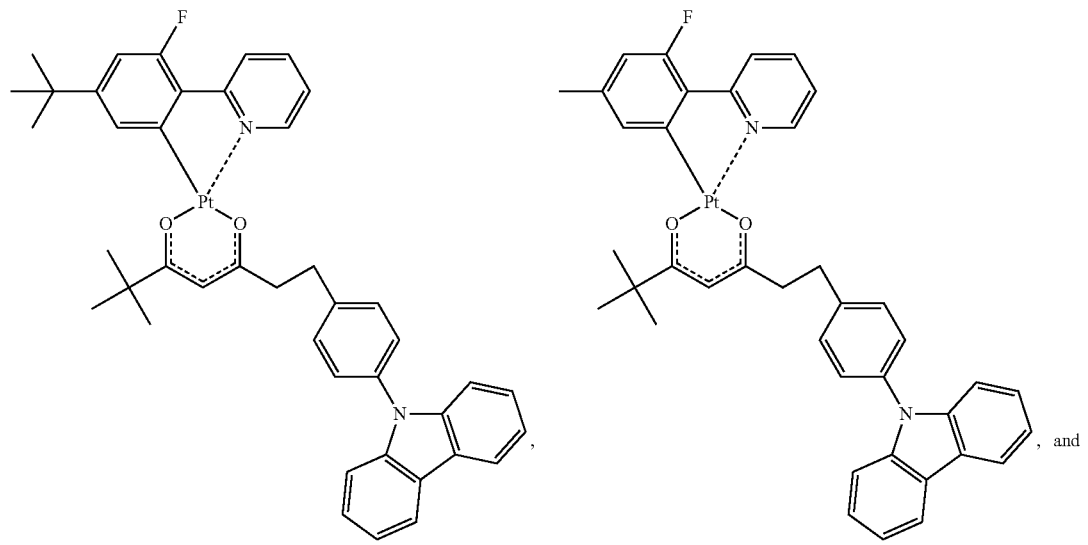

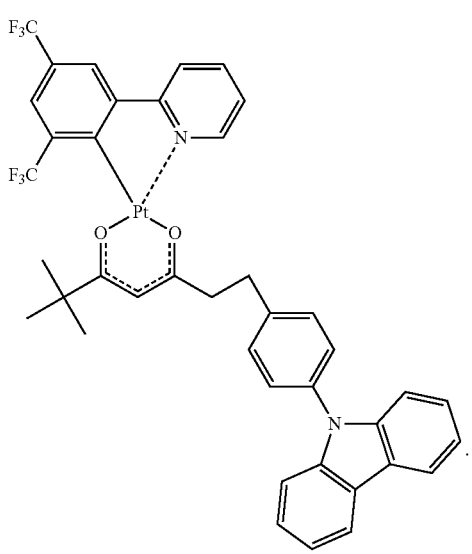

The compounds and compositions described herein can be incorporated into light-emitting devices in various ways. For example, an embodiment provides a light-emitting device comprising: an anode layer comprising a high work function metal; a cathode layer comprising a low work function metal; and a light-emitting layer positioned between, and electrically connected to, the anode layer and the cathode layer. The light-emitting layer comprises the compounds and/or compositions disclosed herein.

The anode layer may comprise a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof, or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). Examples of suitable high work function metals and metal oxides include but are not limited to Au, Pt, or alloys thereof, ITO, IZO, and the like. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In an embodiment, the cathode layer can have a thickness in the range of about 1 nm to about 1000 nm.

The amount of the compounds disclosed herein in the light-emitting composition can vary. In one embodiment, the amount of a compound disclosed herein in the light-emitting layer is in the range of from about 1% to about 100% by weight of the light-emitting layer. In another embodiment, the amount of a compound disclosed herein in the light-emitting layer is in the range of from about 1% to about 10% by weight of the light-emitting layer. In another embodiment, the amount of a compound disclosed herein in the light-emitting layer is about 3% by weight of the light-emitting layer.

The thickness of the light-emitting layer may vary. In one embodiment, the light-emitting layer has a thickness in the range of from about 10 nm to about 200 nm. In another embodiment, the light-emitting layer has a thickness in the range of about 10 nm to about 150 nm.

In another embodiment, the light-emitting layer may also be configured to emit white light.

The compounds and compositions described herein may be useful in an emissive layer without requiring any additional hole-transport or electron-transport materials. Thus, in some embodiments, the light-emitting layer consists essentially of a compound disclosed herein. In other embodiments, the emissive layer comprises a host material and at least one of the emissive compounds disclosed herein. If there is a host material, the amount of the emissive compound with respect to the host material may be any amount suitable to produce adequate emission. In some embodiments, the emissive compound is present at an amount of in the range of from about 0.1% (w/w) to about 10% (w/w), from about 0.1% (w/w) to about 5% (w/w), about 2% (w/w) to about 6% (w/w), or about 4% (w/w), with respect to the weight of the host.

The host in the emissive layer may be at least one of: one or more hole-transport materials, one or more electron-transport materials, and one or more ambipolar materials, which are materials understood by those skilled in the art to be capable of transporting both holes and electrons.

In some embodiments, the hole-transport material comprises at least one of an aromatic-substituted amine, a carbazole, a polyvinylcarbazole (PVK), e.g. poly(9-vinylcarbazole); N,N'-bis(3-methyl-phenyl)N,N'-diphenyl-[1,1'-biphenyl]-4,4'-diamine (TPD); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; 1,1-Bis(4-bis(4-methylphenyl) aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-Tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (α-NPD); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); poly(9-vinylcarbazole) (PVK); a benzidine; a phenylenediamine; a phthalocyanine metal complex; a polyacetylene; a polythiophene; a triphenylamine; an oxadiazole; copper phthalocyanine; N,N'N"-1,3,5-tricarbazoloylbenzene (tCP); N,N'-bis(4-butylphenyl)-N,N'-bis(phenyl)benzidine; and the like.

In some embodiments, the electron-transport material comprises at least one of 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device comprises no electron transport or hole transport layer. In some embodiments, the device consists essentially of the anode layer, the cathode layer, and the light-emitting layer. In other embodiments, the light-emitting device may further comprise a hole-transport layer disposed between the anode and the light-emitting layer. The hole-transport layer may comprise at least one hole-transport material. Suitable hole-transport materials may include those listed above in addition to any others known to those skilled in the art.

In some embodiments, the light-emitting device may further comprise an electron-transport layer disposed between the cathode and the light-emitting layer. The electron-transport layer may comprise at least one electron-transport material. Suitable electron transport materials include those listed above and any others known to those skilled in the art.

If desired, additional layers may be included in the light-emitting device. These additional layers may include an electron injection layer (EIL), a hole blocking layer (HBL), an exciton blocking layer (EBL), and/or a hole injection layer (HIL). In addition to separate layers, some of these materials may be combined into a single layer.

In some embodiments, the light-emitting device can include an electron injection layer between the cathode layer and the light emitting layer. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl) aminophenyl)-cyclohexane.

In some embodiments, the light-emitting device can include an exciton blocking layer, e.g., between the light-emitting layer and the anode. In an embodiment, the band gap of the material(s) that comprise exciton blocking layer is large enough to substantially prevent the diffusion of excitons. A number of suitable exciton blocking materials that can be included in the exciton blocking layer are known to those skilled in the art. Examples of material(s) that can compose an exciton blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N,N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino) phenyl-1,3,4-oxadiazol-2-yl)benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

Those skilled in the art recognize that the various materials described above can be incorporated in several different layers depending on the configuration of the device. In one embodiment, the materials used in each layer are selected to result in the recombination of the holes and electrons in the light-emitting layer. An example of a device configuration that incorporates the various layers described herein is illustrated schematically in FIG. 1. The electron injection layer (EIL), electron transport layer (ETL), hole blocking layer (HBL), exciton blocking layer (EBL), hole transport layer (HTL), and hole injection layer (HIL) can be incorporated in the light-emitting device using methods known to those skilled in the art (e.g., vapor deposition).

The emissive compositions may be prepared by adapting methods known in the art for other emissive compositions. For example, the emissive compositions may be prepared by dissolving or dispersing the emissive compound in a solvent and depositing the compound on the appropriate layer of the device. The liquid may be a single phase, or may comprise one or more additional solid or liquid phases dispersed in it. The solvent may then be allowed to evaporate, or the solvent may be removed via heat or vacuum, to provide an emissive composition. If a host is present, it may be dissolved or dispersed in the solvent with the emissive device and treated as explained above. Alternatively, the compound may be added to a molten or liquid host material, which is then allowed to solidify to provide a viscous liquid or solid emissive composition.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein can be deposited on the anode. The cathode layer, comprising a low work functioning metal (e.g., Mg:Ag), can then be deposited, e.g., vapor evaporated, onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

In some embodiments, the OLED is configured by a wet process such as a process that comprises at least one of spraying, spin coating, drop casting, inkjet printing, screen printing, etc. Some embodiments provide a composition which is a liquid suitable for deposition onto a substrate. The liquid may be a single phase, or may comprise one or more additional solid or liquid phases dispersed in it. The liquid typically comprises a light-emitting compound, a host material disclosed herein and a solvent.

Example 1

Compound Synthesis

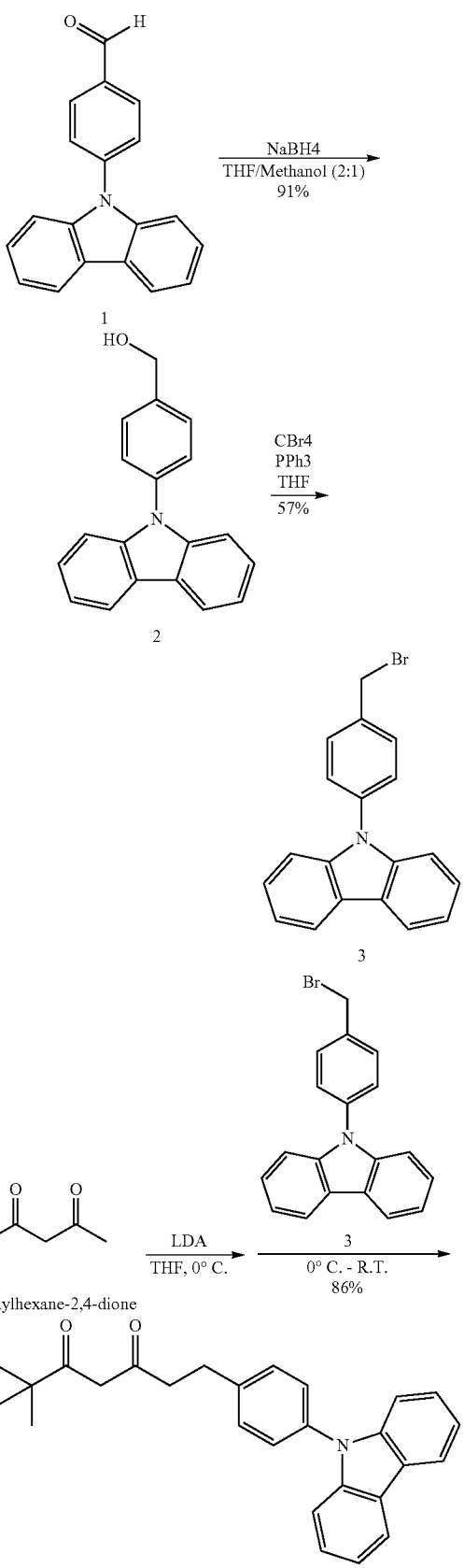

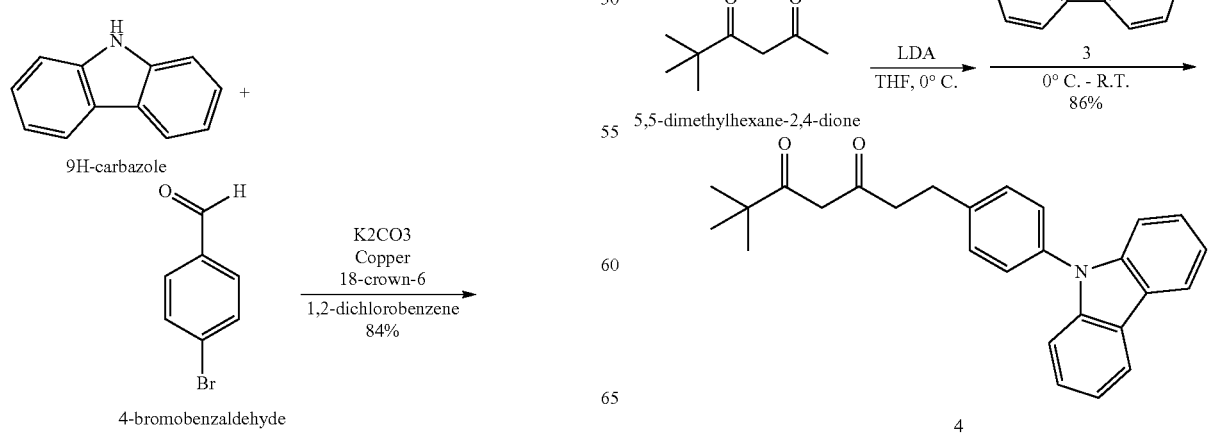

Example 1.1.1

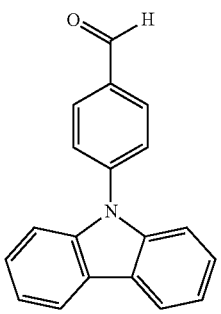

4-(9H-carbazol-9-yl)benzaldehyde (1)

9H-carbazole (30.0 g, 179.4 mmol), 4-bromobenzaldehyde (36.5 g, 197.4 mmol), potassium carbonate (109.1 g, 789.5 mmol), and 18-crown-6 (4.7 g 17.9 mmol) were dissolved in 1,2-dicholorobenzene. The reaction mixture was degassed with argon and then copper (29.9 g, 466.5 mmol) was added. The reaction was heated to about 200° C. under argon for about 36-40 hours. The copper, potassium carbonate, and 18-crown-6 were then filtered off. The solvent was removed and the resulting residue was purified by a silica chromatography, employing 1:1 dichloromethane:hexanes as an eluent. A recrystallization was performed in tetrahydrofuran (THF)/methanol to yield the product 1 as tan solid (84% yield). $^1$H NMR (400 MHz, DMSO-d): δ 10.13 (s, 1H), 8.27 (d, J=7.7 Hz, 2H), 8.20 (d, J=8.4 Hz, 2H), 7.90 (d, J=8.4 Hz, 2H), 7.52 (d, J=8.1 Hz, 2H), 7.48-7.44 (m, 2H), 7.33 (t, J=7.0 Hz, 2H)

Example 1.1.2

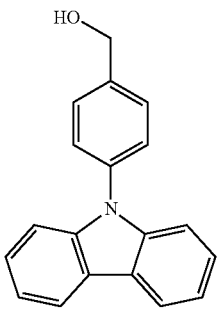

4-(9H-carbazol-9-yl)phenyl)methanol (2)

4-(9H-carbazol-9-yl)benzaldehyde (1) (8.0 g, 29.5 mmol) was dissolved in a (2:1) mixture of tetrahydrofuran/methanol. Sodium borohydride (1.4 g, 38.3 mmol) was added portion wise to the reaction mixture. The reaction mixture was stirred for about 1.5 hours at room temperature and the solvents were then removed. Deionized water was then added to the crude material, and 1M HCl was added dropwise until the solution was neutral. The material was then extracted with ethyl acetate and washed with water. The ethyl acetate was then removed and the product 2 was precipitated out of dichloromethane/hexanes to yield white solid 2 (91% yield). $^1$H NMR (400 MHz, DMSO-d): δ 8.25 (d, J=7.7 Hz, 2H), 7.60 (dd, J$_1$=8.4 Hz, J$_2$=20.2 Hz, 4H), 7.45-7.41 (m, 2H), 7.35 (d, J=8.4 Hz, 2H), 7.28 (t, J=7.0 Hz, 2H), 5.42-5.40 (m, 1H), 4.65 (d, J=5.5 Hz, 2H)

Example 1.1.3

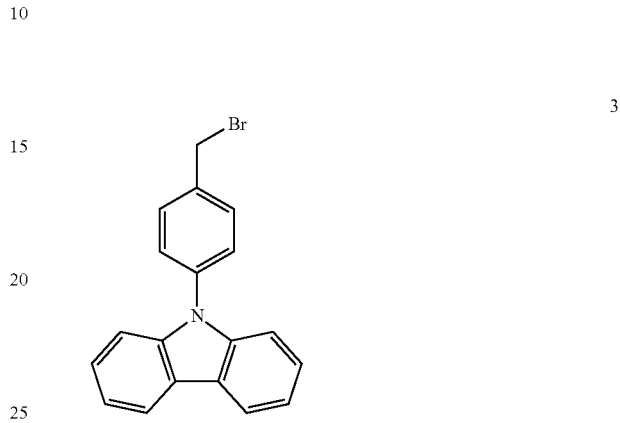

9-(4-(bromomethyl)phenyl)-9H-carbazole (3)

4-(9H-carbazol-9-yl)phenyl)methanol (2) (11.5 g, 41.9 mmol) and carbon tetrabromide (20.9 g, 62.8 mmol) were dissolved in tetrahydrofuran. The reaction mixture was placed in an ice bath. Triphenylphosphine (23.0 g, 87.9 mmol) was dissolved in minimal amount of tetrahydrofuran and then added, via a syringe, slowly into the reaction mixture. The resulting reaction mixture was then slowly brought to room temperature and stirred for about 1.5 hours under argon pressure. The solvent was then removed and the crude product was then purified by silica chromatography (silica) employing 1:4 ethyl acetate:hexanes as the eluent. The crude product was recrystallized in dichloromethane/hexanes to yield the product 3 as a white solid (57% yield). The product 3 was stored under argon, wrapped in foil, and in a freezer to prevent decomposition. $^1$H NMR (400 MHz, DMSO-d) δ 8.25 (d, J=7.68 Hz, 2H), 7.75 (d, J=6.96 Hz, 2H), 7.63 (d, J=6.6 Hz, 2H), 7.44-7.40 (m, 4H), 7.32-7.28 (m, 2H), 4.87 (s, 2H)

Example 1.1.4

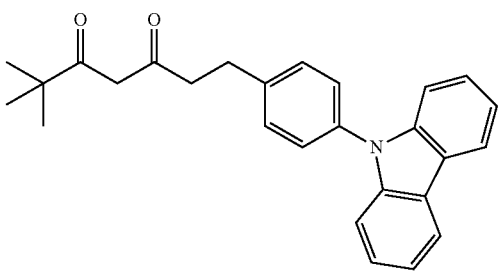

1-(4-(9H-carbazol-9-yl)phenyl)-6,6-dimethylheptane-3,5-dione (4)

5,5-dimethylhexane-2,4-dione (5.37 mL, 35.58 mmol) was dissolved in tetrahydrofuran (5 mL) and the reaction mixture was cooled to about 0° C. in an ice bath. Lithium diisopropylamine (2.0M in heptane, THF, and ethylbenzene, 39.14 mL, 78.28 mmol) was added dropwise and the reaction mixture was then stirred at about 0° C. for 2 hours. 9-(4-(bromomethyl)phenyl)-9H-carbazole (3) (7.97 g, 23.72 mmol) in tetrahydrofuran (20 mL) was added to the reaction mixture and allowed to warm to room temperature overnight. The reaction mixture was then poured into water, acidified with dilute hydrochloric acid and then extracted with ethyl acetate. The solvent was then removed and the crude product was purified by a short silica plug with 1:1 dichloromethane:hexanes as the eluent. The crude product was then recrystallized from methanol to recover an off white solid 4 (86% yield). $^1$H NMR (400 MHz, CDCl$_3$): δ 8.15 (d, J=7.7 Hz, 2H), 7.47-7.49 (m, 2H), 7.39-7.44 (m, 6H), 7.26-7.30 (m, 2H), 5.62 (s, 1H), 3.09 (t, J=7.3 Hz, 2H), 2.74 (t, J=7.3 Hz, 2H), 1.18 (s, 9H).

SCHEME 2

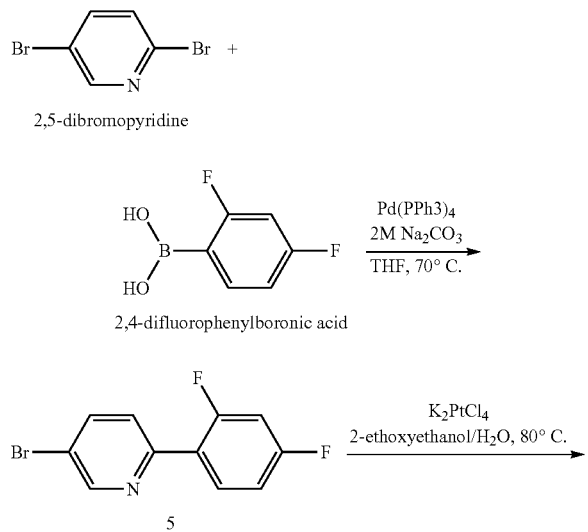

Example 1.2.1

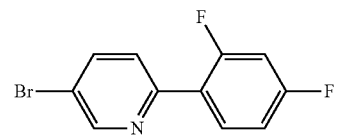

5-bromo-2-(2,4-difluorophenyl)pyridine (5)

2,5-dibromopyridine (5.27 g, 22.24 mmol), 2,4-difluorophenylboronic acid (3.69 g, 23.35 mmol), tetrakis(triphenylphosphine)palladium (771 mg, 0.67 mmol), and sodium carbonate (2M, 22 mL) were added to 36 mL of tetrahydrofuran. The reaction mixture was then bubbled with argon and then heated to about 70° C. overnight. The reaction mixture was then poured into water, then extracted with ethyl acetate and then purified chromatographically to yield a white solid 5 (83% yield) $^1$H NMR (400 MHz, DMSO-d) δ 8.83 (s, 1H), 8.16 (d, J=6.6 Hz, 1H), 7.97 (dd, J$_1$=8.4 Hz, J$_2$=15.8 Hz, 1H), 7.73 (d, J=8.1 Hz, 1H), 7.40 (t, J=9.5 Hz, 1H), 7.24 (t, J=7.3 Hz, 1H).

Example 1.2.2

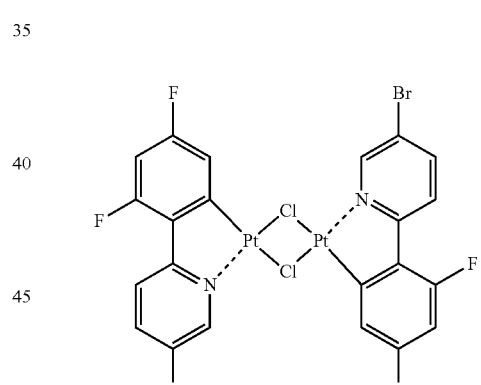

Compound 6:

Adapted from literature ("Synthesis and Characterization of Phosphorescent Cyclometalated Platinum Complexes", Brooks, J., et al., Inorg. Chem.; (2002); 41(12); 3055-3066)). 5-bromo-2-(2,4-difluorophenyl)pyridine (5) (3.9 g, 14.4 mmol), and potassium tetrachloroplatinate (II) (2.7 g, 6.5 mmol) were dissolved in a 3:1 ratio of 2-ethoxyethanol/water. The reaction mixture was heated to about 110° C. under argon pressure for about 20 hours. The reaction mixture was then poured into water and then filtered. The filtrate was then washed with methanol and dried under a vacuum. The crude material was then purified by a short silica plug in 1:4 ethyl acetate: dichloromethane. The solvent was then removed and the resulting crude material was dispersed in methanol and filtered to yield Compound 6 as a yellow solid (57%).

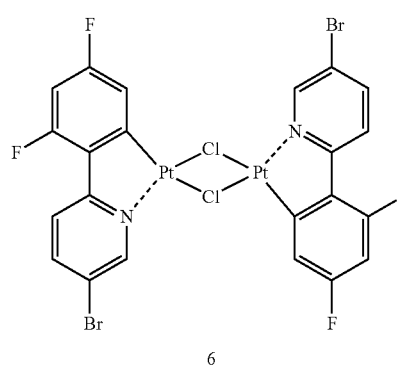

SCHEME 3
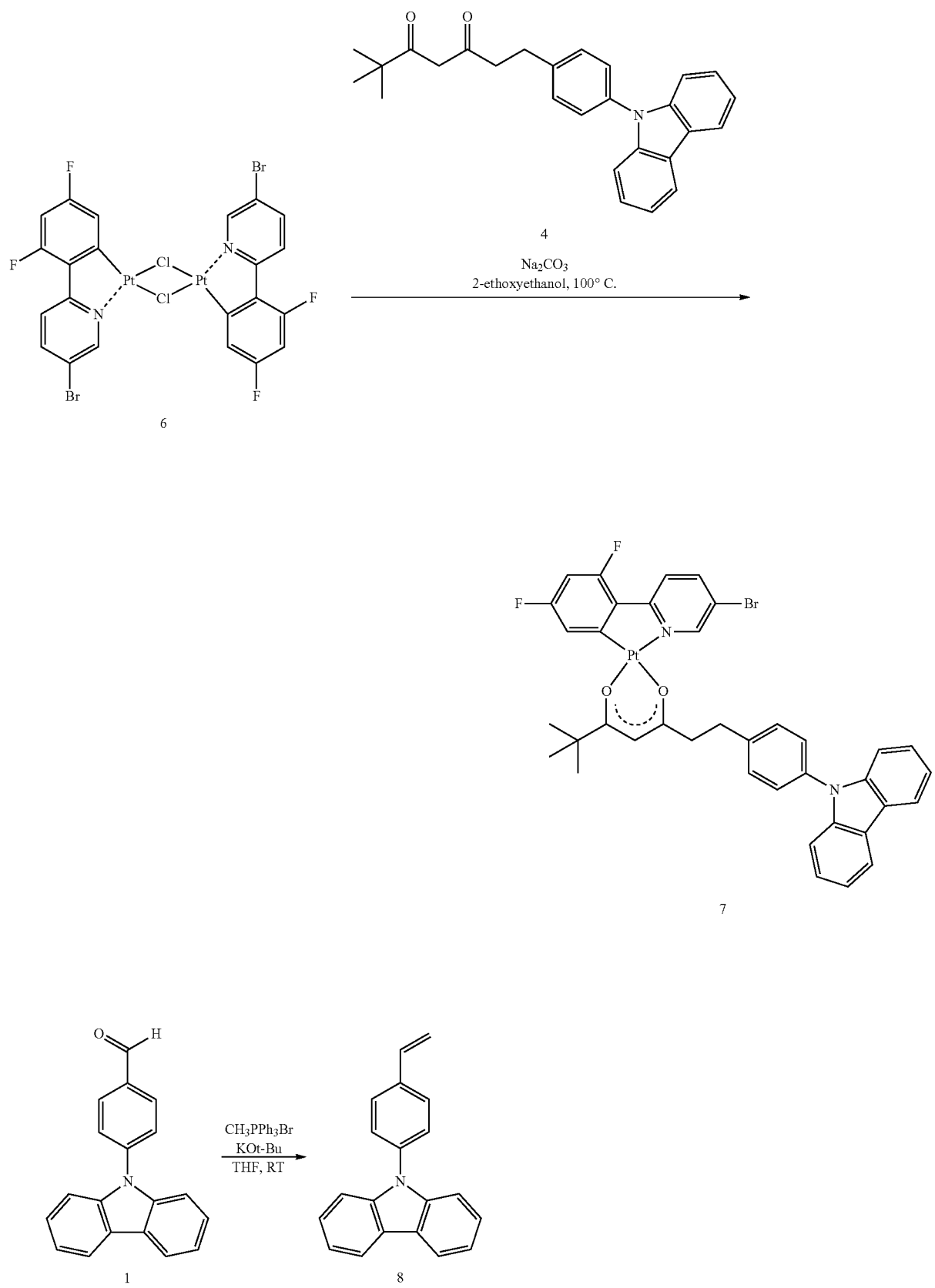

-continued
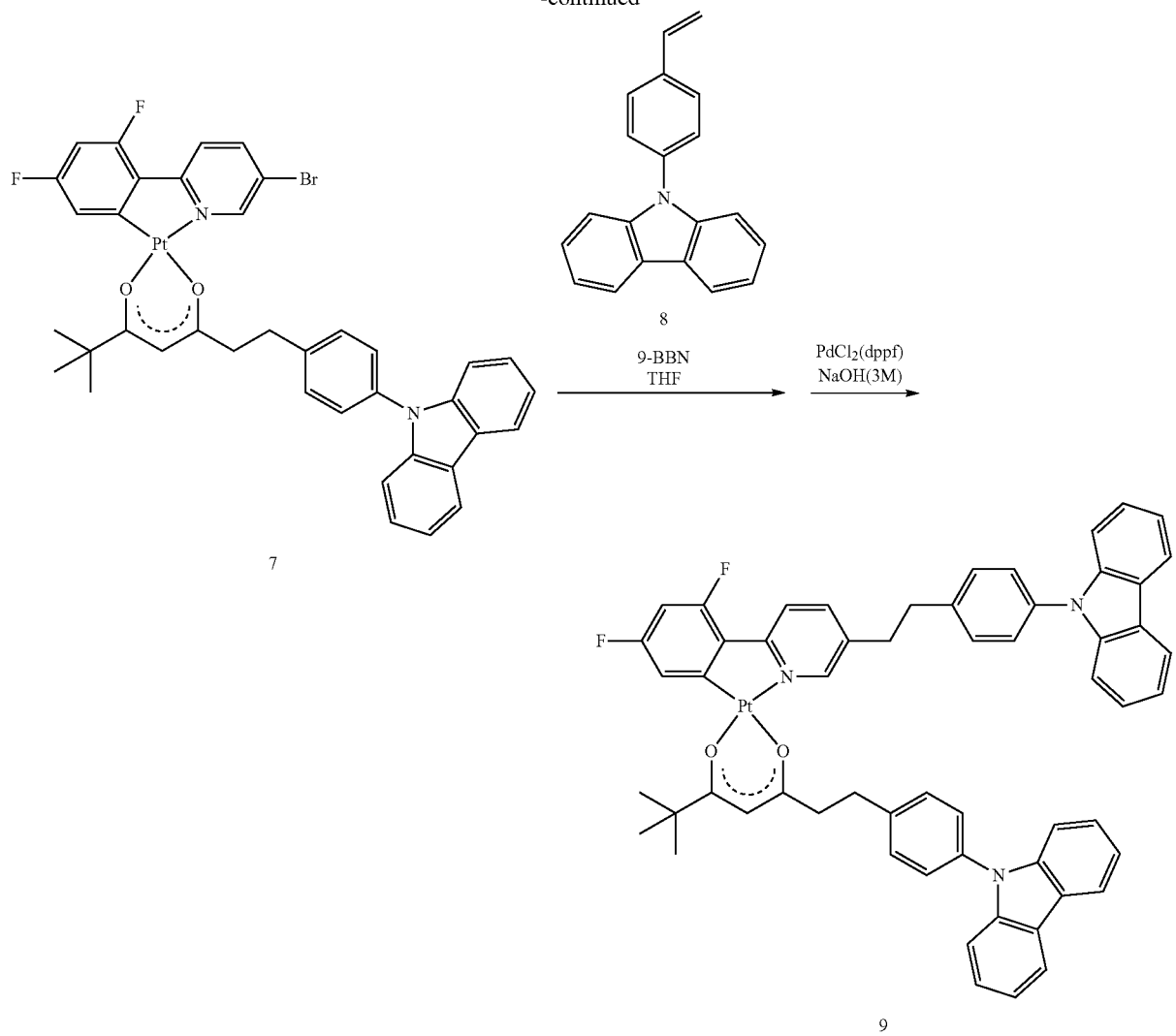
Example 1.3.1
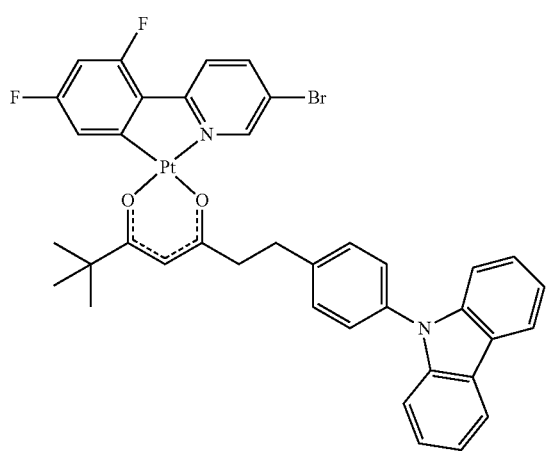
Compound 7:
Dimer 6 (1.640 g, 1.642 mmol), carbazole ligand 4 (1.241 g, 3.119 mmol), NaCO$_3$ (0.87 mg, 8.21 mmol) and 2-ethoxyethanol (25 mL) were heated to about 100° C. overnight. The solvent was removed and the residue was then purified by a short silica plug using 1:1 dichloromethane:hexanes as the eluent and then precipitated out of hexanes to yield a yellow solid 7 (47% yield).
Example 1.3.2
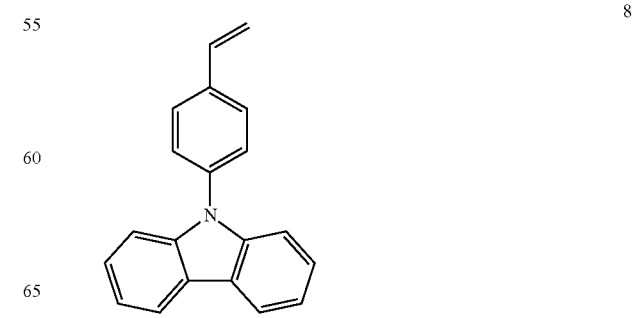

9-(4-vinylphenyl)-9H-carbazole (8)

4-(9H-carbazol-9-yl)benzaldehyde (1) (13.38 g, 49.37 mmol) was dissolved in tetrahydrofuran (200 mL) and then methyltriphenylphosphonium bromide (19.38 g, 54.31 mmol) was added. The reaction mixture was cooled to about 0° C. Potassium t-butoxide was then added. The reaction mixture was stirred at about 0° C. for about 5 minutes, then allowed to warm to room temperature and then stirred overnight. The reaction was then concentrated in vacuo, poured into water, and then extracted with ethyl acetate. The ethyl acetate layer was then dried down and the crude product was run through a silica plug using 1:4 dichloromethane:hexanes to yield an off white solid 8 (44% yield). $^1$H NMR (400 MHz, CDCl$_3$): δ 8.16 (d, J=8.8 Hz, 2H), 7.65 (d, J=8.4 Hz, 2H), 7.54 (d, J=8.4 Hz, 2H), 7.45-7.40 (m, 4H), 7.32-7.29 (m, 2H), 6.84 (dd, J$_1$=17.6 Hz, 3$_2$=10.6 Hz, 1H), 5.87 (d, J=17.2 Hz, 1H), 5.38 (d, J=11.0 Hz, 1H).

Example 1.3.3

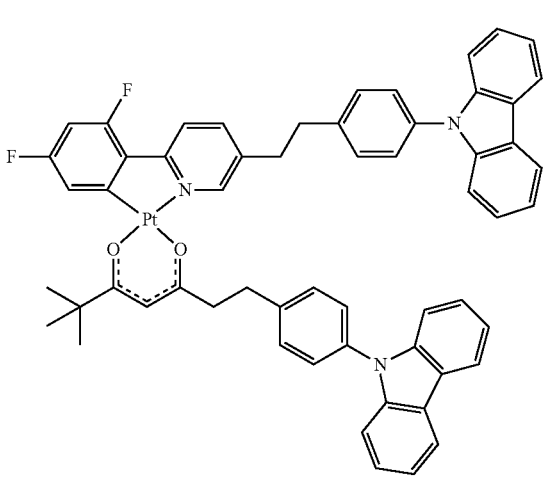

9

Compound 9:
9-(4-vinylphenyl)-9H-carbazole (8) (313 mg, 1.162 mmol) was dissolved in 3 mL anhydrous tetrahydrofuran. 9-Borabicyclo[3.3.1]nonane (0.5M in THF, 7.0 mL) was then added and the solution was then stirred for about 3 hours. Sodium hydroxide (3M, 2.6 mL) and Compound 7 (500 mg, 0.581 mmol) was then added and the reaction mixture was bubbled with argon. [1,1'-Bis(diphenylphosphino)ferrocene]dichloropalladium(II) (21 mg, 0.029 mmol) was then added, the reaction mixture was heated to about 50° C. and stirred overnight. The reaction mixture was then poured into water, extracted with ethyl acetate, and then purified by column chromatography to yield a yellow solid 9 (44% yield). $^1$H NMR (400 MHz, CDCl$_3$): δ 8.90, 8.64 (two m, 1H), 8.12 (m, 4H), 7.94 (m, 1H), 7.68 (m, 1H), 7.48 (m, 2H), 7.37 (m, 8H), 7.27 (m, 10H), 7.16 (m, 1H), 6.61 (m, 1H), 5.62, 5.59 (two s, 1H), 3.22 (m, 1H), 3.09 (m, 2H), 3.00 (m, 3H), 2.72 (m, 1H), 2.57 (m, 1H), 1.28, 1.22 (two s, 9H). MS (MALDI-TOF) m/z calcd. 1050. found, 1050. Anal. calcd. for $C_{58}H_{47}F_2N_3O_2Pt$: C, 66.28; H, 4.41; N, 4.00. Found: C, 66.52; H, 5.36; N, 3.98.

Compounds 11-16

Compounds 11-16 were obtained in a similar manner as Compound 9 from Example 1.1.1 to Example 1.1.3 except, as indicated in Table 1, selected starting diones and substituents (e.g., Examples 1.1.1 to 1.7.4) were employed to obtain the respective dimers and end-products of steps 1.1 1 to step 1.3.4.

TABLE 1

| Compound | Step 1.1.4 | Step 1.3.4 | Step 1.3.1 | Step 1.3.3 |
|---|---|---|---|---|
| Compound 9 | 5,5-dimethylhexane-2,4-dione | Compound 8 | Compound 6 | Compound 8 |
| Comparative Example 1 [FPt1] | Pentane-2,4-dione | None | Compound 23 | None |
| Compound 11 | Pentane-2,4-dione | Compound 8 | Compound 23 | None |
| Compound 12 | 5,5-dimethylhexane-2,4-dione | Compound 8 | Compound 23 | None |
| Compound 13 | 5,5-dimethylhexane-2,4-dione | None | Compound 6 | Compound 8 |
| Compound 14 | 5,5-dimethylhexane-2,4-dione | Compound 31 | Compound 23 | None |
| Compound 15 | 5,5-dimethylhexane-2,4-dione | None | Compound 6 | Compound 27 |
| Compound 16 | 5,5-dimethylhexane-2,4-dione | None | Compound 6 | Compound 26 |

The respective end products were identified as the respective Compound (11-16) from $^1$H-NMR spectrum.

Compound 11

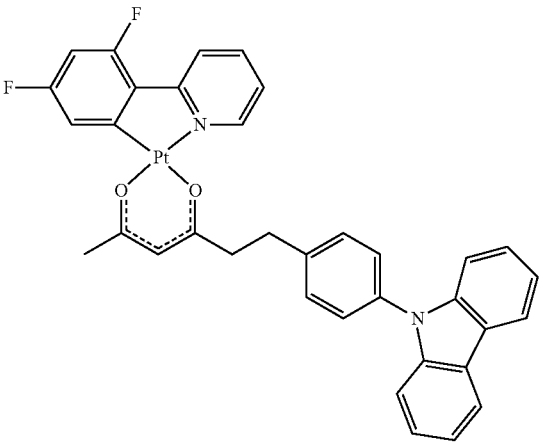

$^1$H NMR (400 MHz, CDCl$_3$): δ 8.90, 8.86 (two d, J=5.5 Hz, 1H), 8.13 (d, J=7.7 Hz, 2H), 7.95 (m, 1H), 7.82 7.73

(two m, 1H), 7.47 (m, 4H), 7.36 (m, 4H), 7.26 (m, 2H), 7.13 (m, 2H), 6.59 (m, 1H), 5.54, 5.52 (two s, 1H), 3.17 (t, J=7.7 Hz, 2H), 2.66 (t, J=7.7 Hz, 2H), 2.04 (s, 3H). MS (MALDI-TOF) m/z calcd. 739. found, 740 [M+H]. Anal. calcd. for $C_{35}H_{26}F_2N_2O_2Pt$: C, 56.83; H, 3.54; N, 3.79. Found: C, 56.48; H, 3.89; N, 3.79.

Compound 12

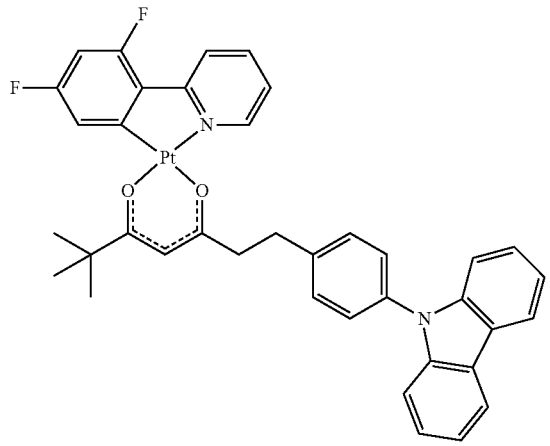

$^1$H NMR (400 MHz, CDCl$_3$): δ 9.02, 8.92 (two d, J=5.5 Hz, 1H), 8.13 (d, J=7.3 Hz, 2H), 7.98 (m, 1H), 7.84, 7.76

Compound 13

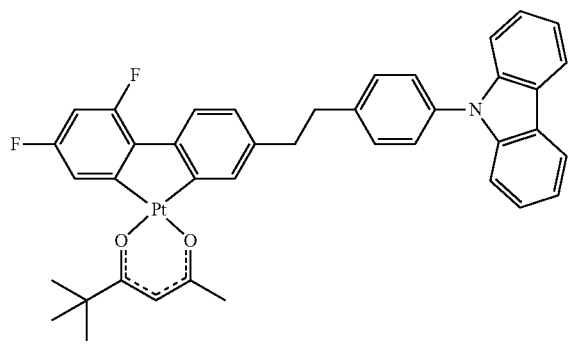

$^1$H NMR (400 MHz, CDCl$_3$): δ 8.87, 8.72 (two s, 1H), 8.13 (d, J=7.7 Hz, 2H), 7.90 (d, J=8.8, 1H), 6.67 (m, 1H), 7.47 (m, 2H), 7.39 (m, 4H), 7.34 (m, 2H), 7.26 (m, 2H), 7.13, (m, 1H), 6.57 (m, 1H), 5.61, 5.56 (two s, 1H), 3.09 (m, 4H), 2.06, 1.94 (two s, 3H), 1.27, 1.22 (two s, 9H). MS (ESI) m/z calcd. 795. found, 796 [M+H]. Anal. calcd. for $C_{39}H_{34}F_2N_2O_2Pt$: C, 58.86; H, 4.31; N, 3.52. Found: C, 58.72; H, 4.70; N, 3.58.

Compound 14

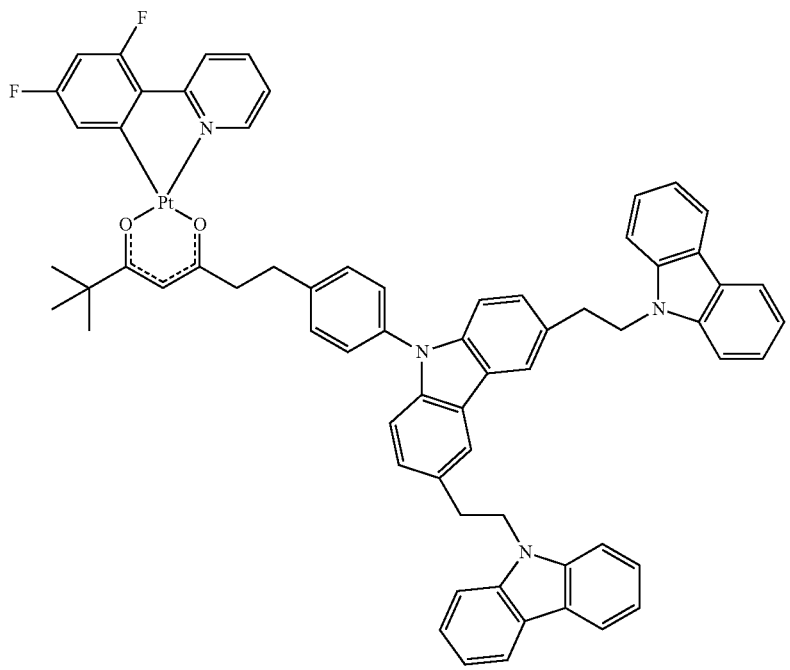

(two m, 1H), 7.47 (m, 4H), 7.36 (m, 4H), 7.26 (m, 2H), 7.15 (m, 2H), 6.60 (m, 1H), 5.67, 5.65 (two s, 1H), 3.20 (t, J=6.7 Hz, 2H), 2.74 (t, J=7.3 Hz, 2H), 1.28-1.26 (two s, 9H). MS (MALDI-TOF) m/z calcd. 781. found, 782 [M+H]. Anal. calcd. for $C_{38}H_{32}F_2N_2O_2Pt$: C, 58.38; H, 4.13; N, 3.58. Found: C, 58.58; H, 4.43; N, 3.66.

$^1$H NMR (400 MHz, CDCl$_3$): δ 9.03, 8.91 (two d, J=5.6 Hz, 1H), 8.13 (d, J=7.7 Hz, 4H), 8.00 (m, 1H), 7.96 (s, 2H), 7.85, 7.72 (two m, 1H), 7.45 (m, 12H), 7.24 (m, 6H), 7.16 (m, 4H), 6.59 (m, 1H), 5.68, 5.66 (two s, 1H), 4.61 (t, J=7.3 Hz, 4H), 3.30 (t, J=7.7 Hz, 4H), 3.20 (m, 2H), 2.74 (m, 2H), 1.28, 1.27 (two s, 9H). Anal. calcd. for $C_{66}H_{54}F_2N_4O_2Pt$: C, 67.86; H, 4.66; N, 4.80. Found: C, 67.60; H, 5.08; N, 4.86.

Compound 15
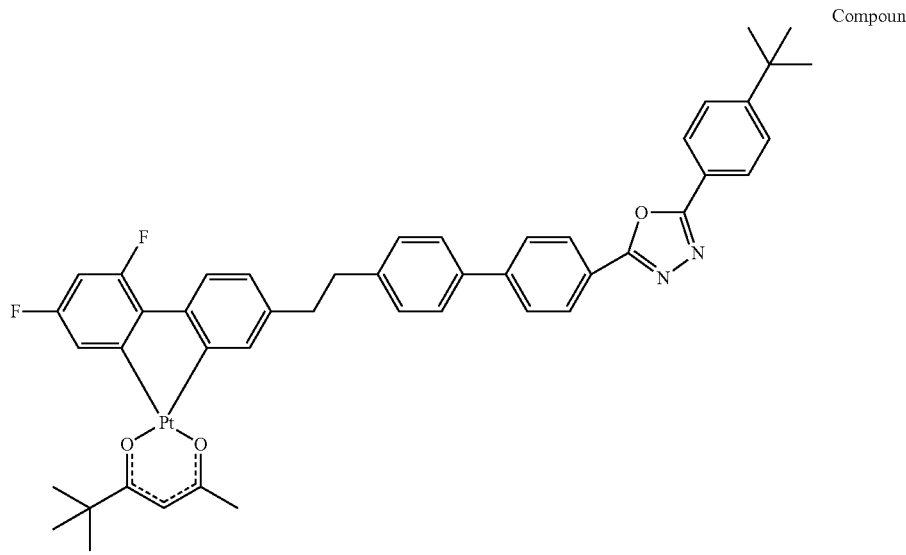
$^{1}$H NMR (400 MHz, CDCl$_{3}$-d): δ 8.90-8.72 (m, 1H), 8.18 (d, J=8.4 Hz, 2H), 8.08 (d, J=8.4 Hz, 2H), 7.86 (d, J=8.8 Hz, 1H), 7.74 (d, J=8.0 Hz, 3H), 7.62-7.53 (m, 6H), 7.12-7.10 (m, 1H), 6.66 (t, J=9.5 Hz, 1H), 5.62 (m, 1H), 3.03 (s, 4H), 2.04 (s, 2H), 1.98 (s, 1H), 1.39 (s, 9H), 1.24 (s, 9H)
Compound 16
$^{1}$H NMR (400 MHz, CDCl$_{3}$-d): δ 8.88 (s, 1H), 8.07-8.04 (m, 4H), 7.85 (d, J=9.2 Hz, 1H), 7.55-7.53 (m, 3H), 7.29 (d, J=8.4 Hz, 2H), 7.11-7.08 (m, 1H), 6.56 (t, J=9.3 Hz, 1H), 5.61 (s, 1H), 3.05-3.03 (m, 4H), 2.04 (s, 3H), 1.36 (s, 9H), 1.24 (s, 9H)
Example 1.4.1
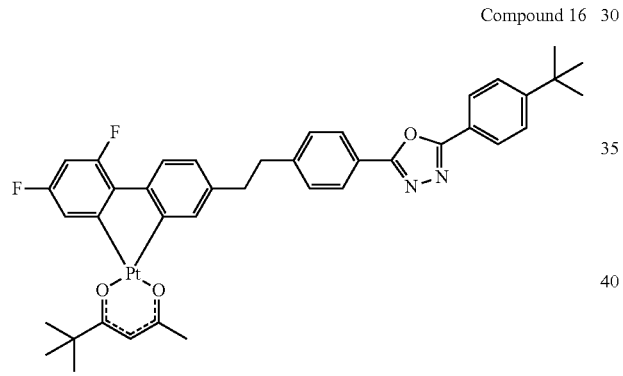
23
Compound 23:
Dimer 23 was prepared by the method of Brooks ("Synthesis and Characterization of Phosphorescent Cyclometalated Platinum Complexes", Brooks, J., et al., Inorg. Chem.; 2002; 41(12); 3055-3066))
SCHEME 4
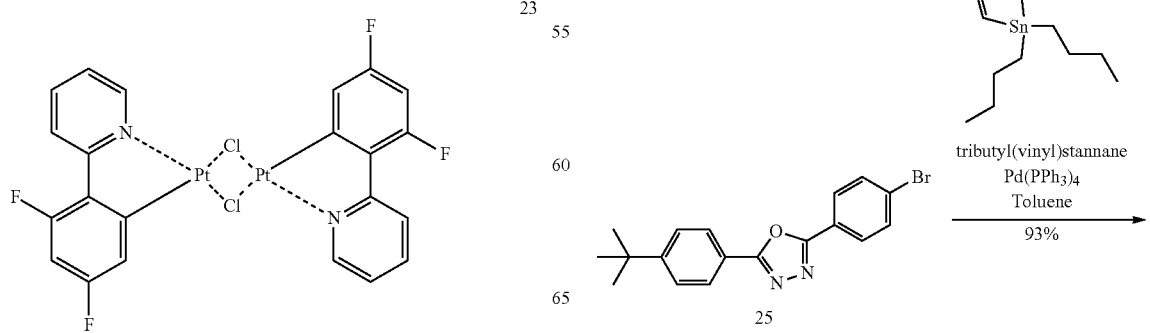

-continued

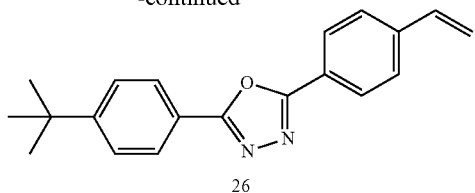

26

Example 1.5.1

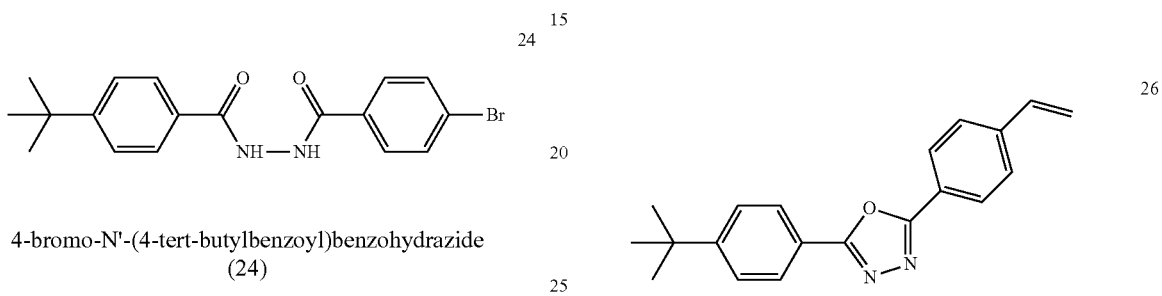

4-bromo-N'-(4-tert-butylbenzoyl)benzohydrazide (24)

4-bromobenzohydrazide (11.0 g, 51.1 mmol) was dissolved in tetrahydrofuran. Pyridine (4.2 g, 53.7 mmol) was then slowly added to the reaction mixture. The reaction mixture was then gently heated to dissolve all of the 4-bromobenzohydrazide. The heated mixture was then cooled to room temperature and then placed in an ice bath. 4-tert-butylbenzoyl chloride (10.6 g, 53.7 mmol) was then slowly added to the flask. The flask was removed from the ice bath and then stirred at room temperature for about 1 hour under argon pressure. The solvent was then removed and the crude material was then placed in a filter and then washed with water. The crude material was then dried in a vacuum oven and purified by a recrystallization in methanol to yield a white solid 24 (92% yield). $^1$H NMR (400 MHz, DMSO-d) δ 10.60 (s, 1H), 10.47 (s, 1H), 7.88-7.85 (m, 4H), 7.76 (d, J=8.8 Hz, 2H), 7.54 (d, J=8.4 Hz, 2H), 1.32 (s, 9H).

Example 1.5.2

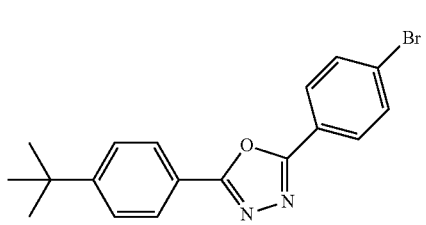

2-(4-bromophenyl)-5-(4-tert-butylphenyl)-1,3,4-oxadiazole (25)

4-bromo-N'-(4-tert-butylbenzoyl)benzohydrazide (24) (18.0 g, 48.01 mmol) and 1-4,dioxone were heated to 115° C. under argon until the material went into solution. The reaction mixture was removed from the heat and cooled slightly. Phosphorus chloride oxide (13.2 mL, 154.3 mmol) was then added to the reaction mixture. The contents of the reaction flask was then removed from under argon and exposed, by t-valve, to sodium bicarbonate to capture the generated hydrogen chloride. The reaction mixture was then heated to about 115° C. for about 30 minutes. The solvent was then removed and in the product extracted with dichloromethane. The product, dissolved in dichloromethane, was then washed with sodium bicarbonate, water, and brine. The dichloromethane was removed and the resulting crude material was then purified by a recrystallization in dichloromethane/hexanes to yield a white solid 25 (79% yield). $^1$H NMR (400 MHz, CDCl$_3$) δ 8.04 (d, J=8.8 Hz, 2H), 7.99 (d, J=8.8 Hz, 2H), 7.65 (d, J=8.4 Hz, 2H), 7.54 (d, J=8.8 Hz, 2H), 1.36 (s, 9H).

Example 1.5.3

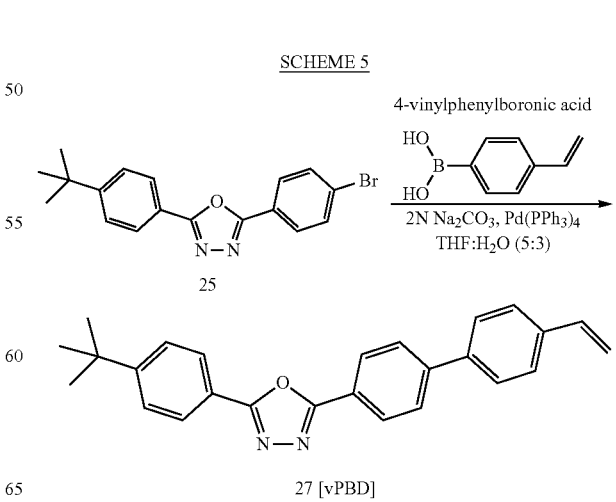

2-(4-tert-butylphenyl)-5-(4-vinylphenyl)-1,3,4-oxadiazole (26)

2-(4-bromophenyl)-5-(4-tert-butylphenyl)-1,3,4-oxadiazole (25) (3.1 g, 8.7 mmol), tributyl(vinyl) stannane (4.5 g, 14.3 mmol), and tetrakis(triphenylphosphine)palladium (300.6 mg, 0.3 mmol) were added to a Schlenk flask and dissolved in a minimal amount of toluene. Four cycles of freeze-pump-thaw were performed and then the reaction mixture was heated to about 65° C. for approximately 85 hours. The crude material was then purified by silica chromatography in dichloromethane in order to remove toluene and then the solvent was changed to 1:4 acetone:hexanes in order to elude the product. The solvents were removed and a recrystallization was performed in dichloromethane/hexanes to yield an off white solid (26) (93% yield), $^1$H NMR (400 MHz, CDCl$_3$): δ 8.10-8.05 (m, 4H), 7.57-7.53 (m, 4H), 6.77 (dd, J$_1$=17.6 Hz, J$_2$=11 Hz, 1H), 5.89 (d, J=17.6 Hz, 1H), 5.39 (d, J=11 Hz, 1H), 1.37 (s, 9H).

SCHEME 5

Example 1.6.1

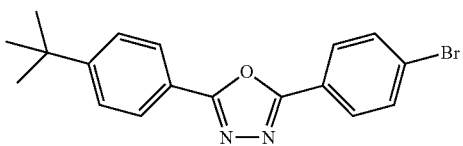

2-(4-bromophenyl)-5-(4-tert-butylphenyl)-1,3,4-oxadiazole (25)

Compound 25 was prepared as described in examples 1.5.1-1.5.2.

Example 1.6.2

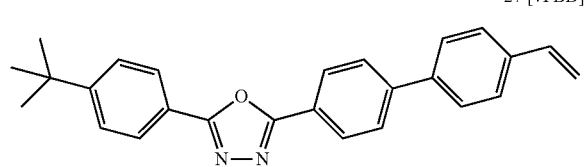

2-(4-tert-butylphenyl)-5-(4'-vinylbiphenyl-4-yl)-1,3,4-oxadiazole (27 [vPBD])

A mixture of 25 (16.01 g, 44.81 mmol), 4-vinylphenylboronic acid (6.745 g, 45.58 mmol), tetrakis(triphenylphosphine)palladium (2.589 g, 2.241 mmol), sodium carbonate (17.00 g, 160.4 mmol), $H_2O$ (143 mL) and THF (240 mL) was degassed with argon for about 1 h while stirring. The reaction mixture was then maintained at about 80° C. with stirring under argon for about 66 h. Upon completion, the reaction was cooled to room temperature and poured over ethylacetate (200 mL). The organic phase was then washed with saturated sodium bicarbonate, water and brine, dried over magnesium sulfate, then filtered and concentrated in vacuo. The crude product was then purified via flash chromatography (silica, 100% dichloromethane to 19:1 dichloromethane-ethyl acetate) to afford 27 (14.8 g, 87% yield) as an off-white crystalline solid. $^1$H NMR (400 MHz, $CDCl_3$): δ 8.20 (d, J=8.8 Hz, 2H), 8.08 (d, J=8.8 Hz, 2H), 7.76 (d, J=8.4 Hz, 2H), 7.63 (d, J=8.4 Hz, 2H), 7.60-7.51 (m, 4H), 6.77 (dd, $J_1$=17.6 Hz, $J_2$=11.0 Hz, 1H), 5.83 (d, J=18.0 Hz, 1H), 5.31 (d, J=11.4 Hz, 1H), 1.36 (s, 9H)

SCHEME 6

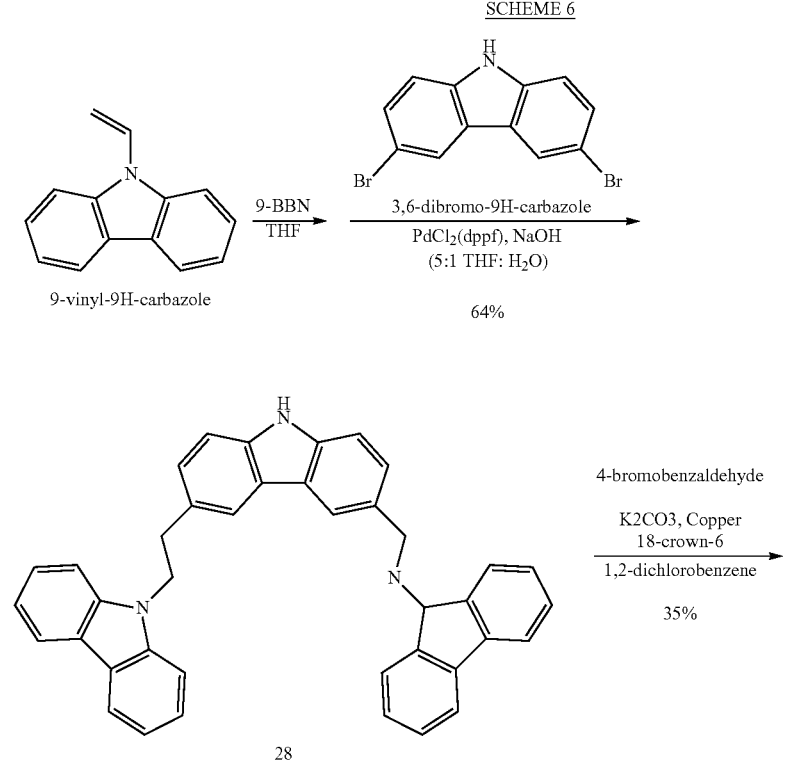

28

3,6-bis(2-(9H-carbazol-9-yl)ethyl)-9H-carbazole

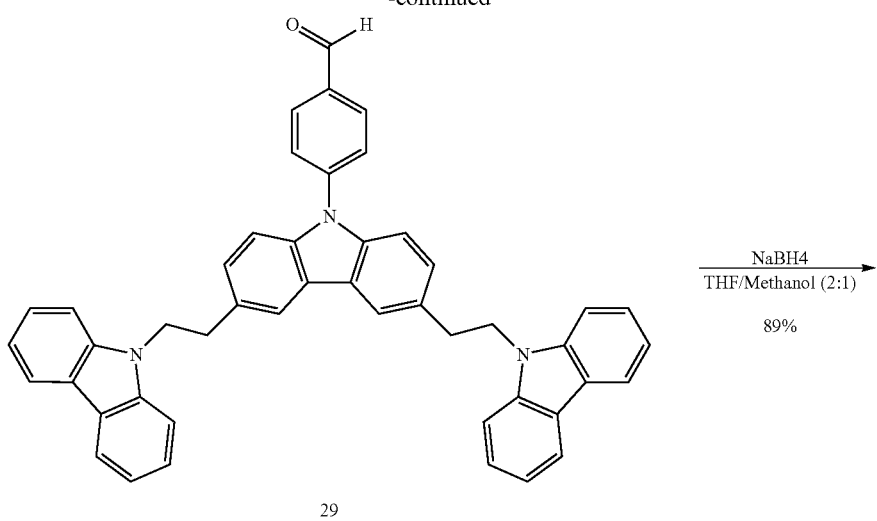
29
4-(3,6-bis(2-(9H-carbazol-9-yl)ethyl)-9H-carbazol-9-yl)benzaldehyde
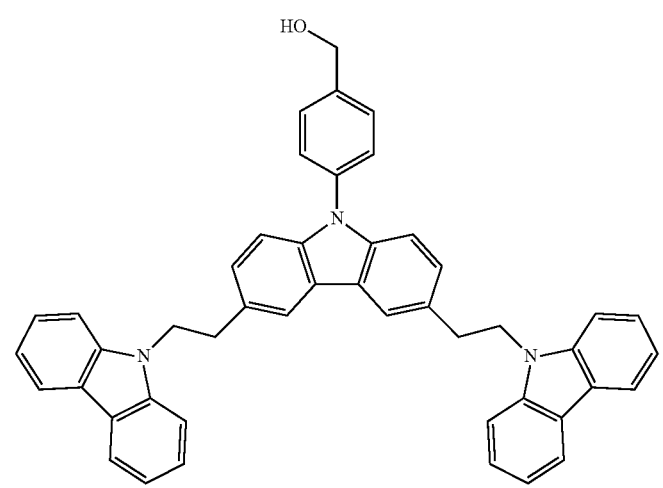
30
(4-(3,6-bis(2-(9H-carbazol-9-yl)ethyl)-9H-carbazol-9-yl)phenyl)methanol
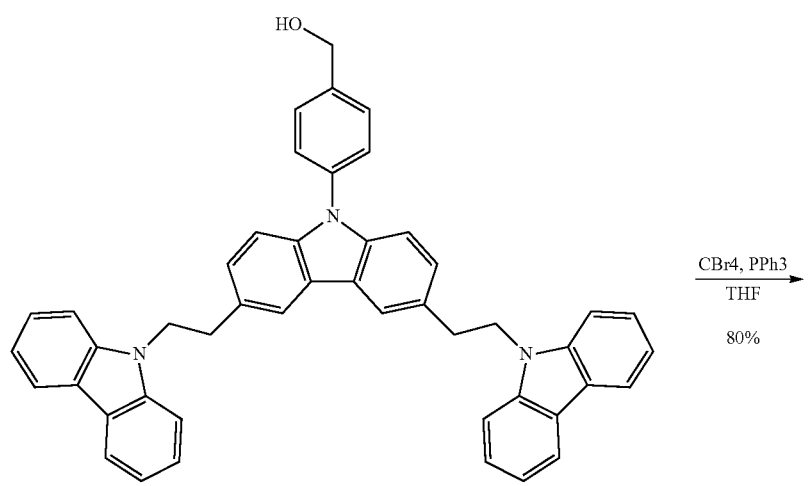
30
(4-(3,6-bis(2-(9H-carbazol-9-yl)ethyl)-9H-carbazol-9-yl)phenyl)methanol

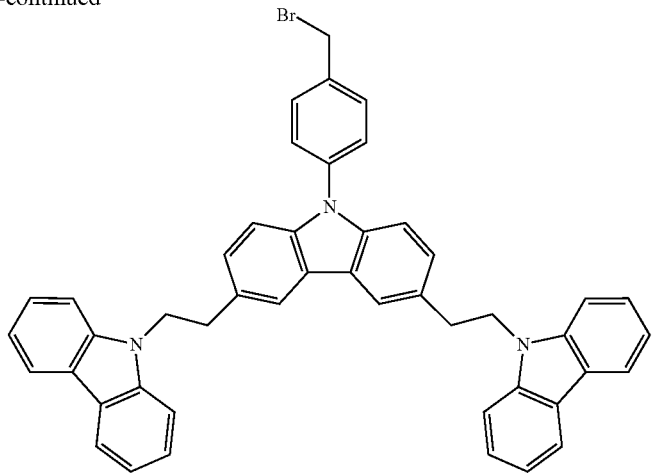

31

9,9'-(2,2'-(9-(4-(bromomethyl)phenyl)-9H-carbazole-3,6-diyl)bis(ethane-2,1-diyl))bis(9H-carbazole)

Example 1.7.1

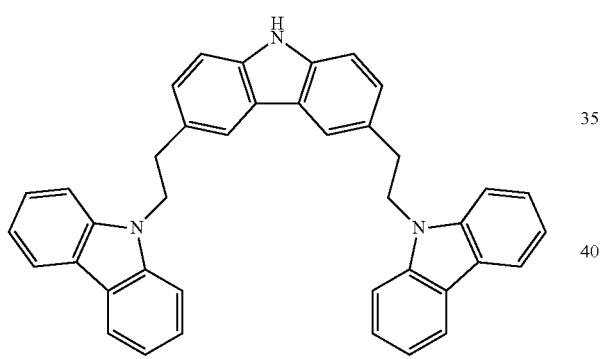

3,6-bis(2-(9H-carbazol-9-yl)ethyl)-9H-carbazole (28)

9-vinyl-9H-carbazole (27.0 g, 138.5 mmol) was dissolved in tetrahydrofuran and placed into an ice bath. 9-Borabicyclo[3.3.1]nonane (840.0 mL, 415.4 mmol) was added via a cannula to the reaction mixture. The reaction mixture was slowly brought to room temperature and stirred for about 3 hours under argon pressure. Sodium hydroxide (3M solution, 30.0 g, 750.0 mmol) was then added slowly into the reaction mixture. An additional amount of tetrahydrofuran was added to make the overall ratio of tetrahydrofuran to water 5:1. 3,6-Dibromo-9H-carbazole (15.1 g, 46.2 mmol) was then added to the reaction mixture. The reaction mixture was then degassed with argon for approximately one hour, and 1,1'-bis(diphenylphosphino)ferrocene]dichloropalladium(II) (1.0 g, 1.4 mmol) was added. The reaction mixture was then heated to about 50° C. overnight under argon pressure. The solvent was then removed, and the resulting residue was extracted with ethyl acetate and washed with water and brine. The ethyl acetate was then removed and the crude product was first purified by silica chromatography with 2:3 dichloromethane:hexanes as the eluent. The crude material was then purified by columns in both 2:3 dichloromethane:hexanes and 1:9 ethyl acetate:hexanes to remove the bottom and top spots impurities, respectively, to yield the product as a white solid 28 (64% yield). $^1$H NMR (400 MHz, DMSO-d): δ 11.05 (s, 1H), 8.16 (d, J=7.7 Hz, 4H), 8.10 (s, 2H), 7.68 (d, J=8.0 Hz, 4H), 7.47-7.43 (m, 4H), 7.40-7.31 (m, 4H) 7.20 (t, J=7.2 Hz, 4H), 4.70-4.66 (m, 4H), 3.19 (t, J=7.7 Hz, 4H)

Example 1.7.2

Compound 29

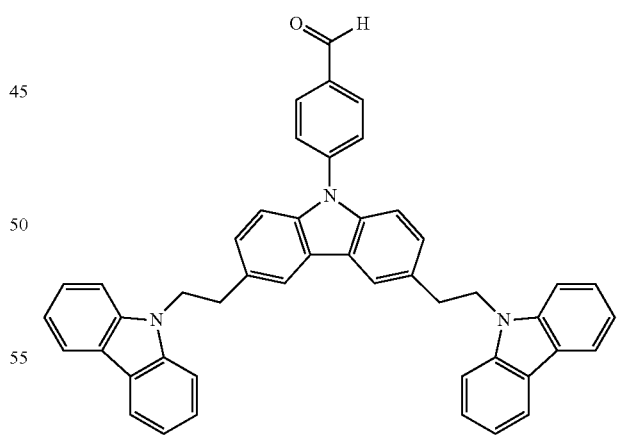

3,6-bis(2-(9H-carbazol-9-yl)ethyl)-9H-carbazole-9-carbaldehyde (29)

3,6-bis(2-(9H-carbazol-9yl)ethyl)-9H-carbazole (28) (8.0 g, 14.4 mmol) 4-bromobenzaldehyde (8.0 g, 43.2 mmol), potassium carbonate (10.8 g, 77.8 mmol), and 18-crown-6 (76 mg, 0.3 mmol) were dissolved in 1,2-dicholorobenzene.

The reaction mixture was degassed with argon and then copper (3 g, 46.8 mmol) was added. The reaction mixture was heated to about 200° C. under argon for about 72 hours. The copper, potassium carbonate, and 18-crown-6 were then filtered off. The solvent was removed and the resulting residue was first purified by a short silica plug with 1:1 dichloromethane:hexanes as the eluent. A precipitation in methanol was performed as well as a silica column in 1:9 ethyl acetate:hexanes to yield the product 29 as pale yellow solid (35%). $^1$H NMR (400 MHz, CDCl$_3$): δ 10.1 (s, 1H), 8.12 (d, J=8.1 Hz, 6H), 7.92 (s, 2H), 7.73 (d, J=8.4 Hz, 2H), 7.46-7.37 (m, 10H), 7.26-7.20 (m, 6H), 4.62 (t, J=7.5 Hz, 4H), 3.32 (t, J=7.5 Hz, 4H).

Example 1.7.3

Compound 30

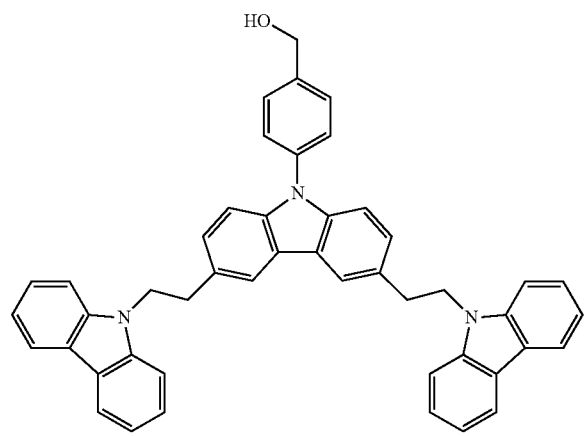

(3,6-bis(2-(9H-carbazol-9-yl)ethyl)-9H-carbazol-9-yl)methanol (30)

3,6-bis(2-(9H-carbazol-9-yl)ethyl)-9H-carbazole-9-carbaldehyde (29) (2.5 g, 3.8 mmol) was dissolved in a (2:1) mixture of tetrahydrofuran/methanol. Sodium borohydride (186.8 mg, 4.9 mmol) was added portion wise to the reaction mixture. The reaction mixture was stirred for two hours at room temperature and the solvents were then removed. To the crude material was added deionized water and 1M HCl was added dropwise until the solution was neutral. The desired material was extracted with dichloromethane and washed with water. The dichloromethane was removed and silica chromatography was performed with 1:1 dichloromethane:hexanes as the eluent. The solvents were removed and the product was precipitated out of dichloromethane/hexanes to yield an off white solid product 30 (89% yield). 1H NMR (400 MHz, DMSO-d): δ 8.23 (s, 2H), 8.16 (d, J=7.7 Hz, 4H), 7.69 (d, J=8.0 Hz, 4H), 7.62 (d, J=8.1 Hz, 2H), 7.51 (d, J=8.0 Hz, 2H), 7.47 (t, J=7.3 Hz, 4H), 7.40 (d, J=8.4 Hz, 2H), 7.26 (d, J=8.4 Hz, 2H), 7.21 (t, J=7.5 Hz, 4H), 5.42-5.40 (m, 1H), 4.69-4.64 (m, 6H), 3.22 (t, J=7.5 Hz, 4H).

Example 1.7.4

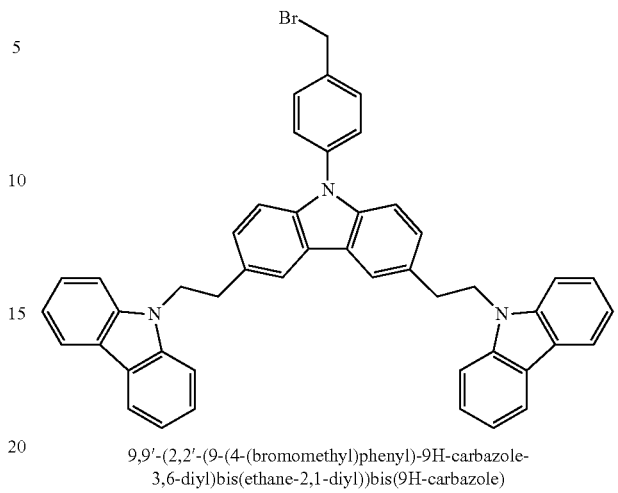

9,9'-(2,2'-(9-(4-(bromomethyl)phenyl)-9H-carbazole-3,6-diyl)bis(ethane-2,1-diyl))bis(9H-carbazole) 31

9,9'-(2,2'-(9-(bromomethyl)-9H-carbazole-3,6-diyl)bis(ethane-2,1-diyl))bis(9H-carbazole) (31)

(3,6-bis(2-(9H-carbazol-9-yl)ethyl)-9H-carbazol-9-yl)methanol (30) (2.0 g, 3.0 mmol) and carbon tetrabromide (1.7 g, 5.1 mmol) were dissolved in tetrahydrofuran. Triphenylphosphine (1.4 g, 5.5 mmol) was dissolved in a minimal amount of tetrahydrofuran and then added, via a syringe, slowly into the reaction mixture. The reaction was stirred at room temperature for 7 hours under argon pressure and then was placed in the freezer overnight. After the reaction was removed from the freezer, the reaction was stirred for additional 1 hour at room temperature. The solvent was removed and the crude product was purified by silica chromatography with 1:1 dichloromethane:hexanes as the eluent. The product was then precipitated from dichloromethane/hexane as an off white solid 31 (80% yield). $^1$H NMR (400 MHz, DMSO-d) δ 8.22 (s, 2H), 816 (d, J=8.1 Hz, 4H), 7.74 (d, J=8.4 Hz, 2H), 7.69 (d, J=8.0 Hz, 4H), 7.57 (d, J=8.4 Hz, 2H), 7.48-7.44 (m, 4H), 7.39 (d, J=8.4 Hz, 2H), 7.30 (d, J=8.4 Hz, 2H), 7.21 (t, J=7.5 Hz, 4H), 4.86 (s, 2H), 4.69 (t, J=7.5 Hz, 4H), 3.22 (t, J=7.7 Hz, 4H).

SCHEME 7

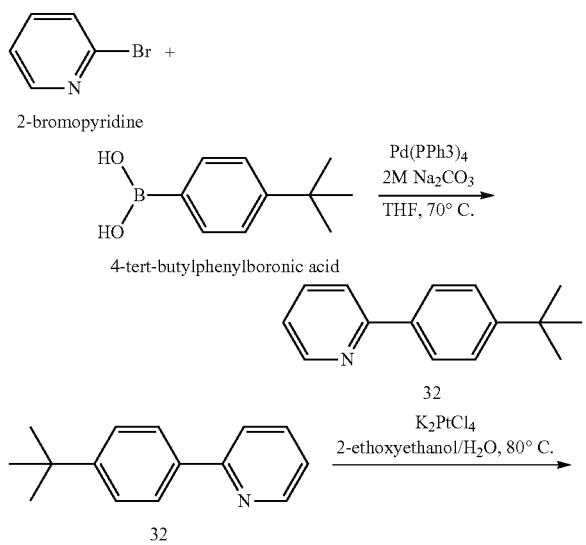

Example 1.10.1

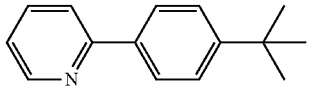

32

Tetrakis(triphenylphosphine)palladium(0) (117 mg, 0.10 mmol) was added to a solution of 4-tert-butylphenylboronic acid (1.0 g, 5.6 mmol) and 2-bromopyridine (807 mg, 5.1 mmol) in toluene (20 mL), an aqueous solution of 2M K2CO3 (10 mL) and ethanol (5 mL) under argon atmosphere. The resulting mixture was stirred for about 15 h at about 70° C. After the palladium catalyst was removed by filtration, the solvent was removed under reduced pressure. The residue was purified by column chromatography on silica gel (dichloromethane) to give 2-(4-tert-butylphenyl)pyridine 32 as colorless oil (210 mg, 99%). TLC Rf=0.50 (dichloromathene); 1H NMR (CDCl$_3$) δ 1.36 (s, 9H), 7.16-7.22 (m, 1H), 7.49 (d, 2H, J=6.6 Hz), 7.69-7.76 (m, 2H), 7.92 (d, 2H, J=6.6 Hz).

Example 1.10.2

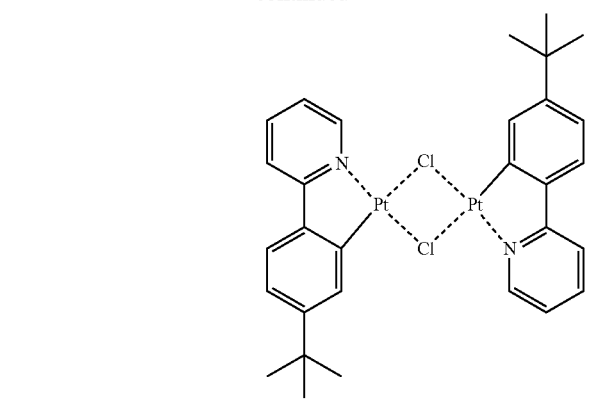

33

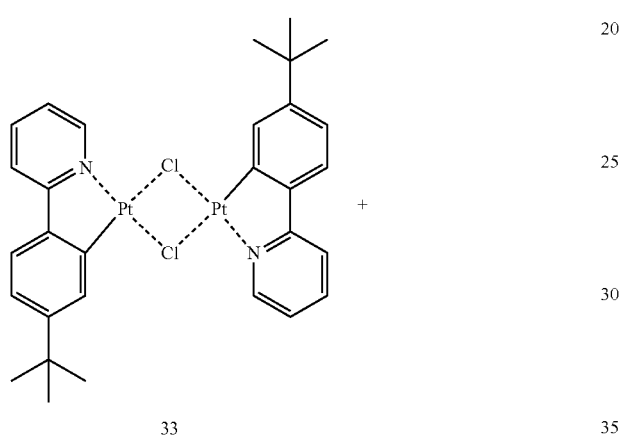

33

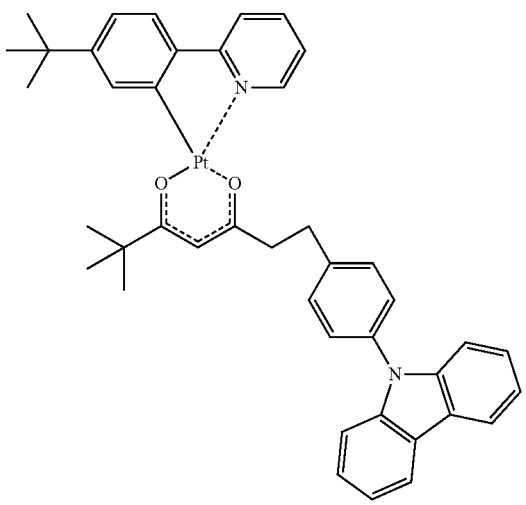

17

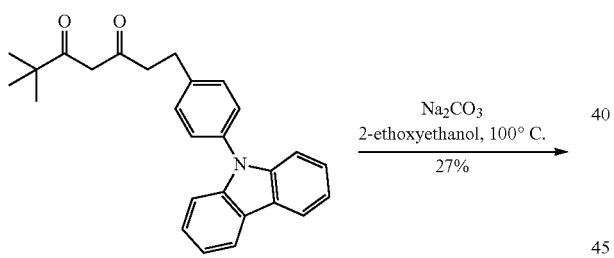

4

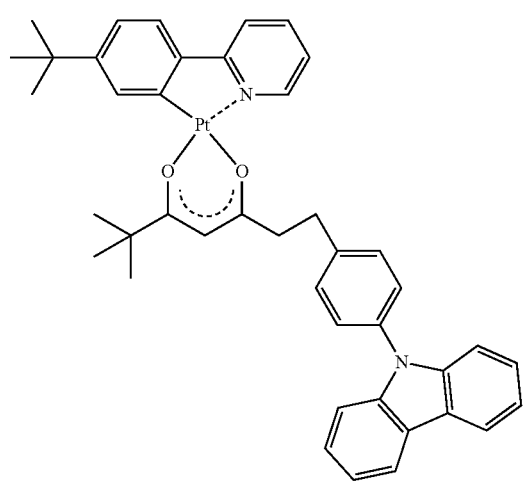

17

The mixture of potassium tetrachloroplatinate(II) (500 mg, 1.2 mmol) and 2-(4-tert-butylphenyl)pyridine 32 (760 mg, 3.6 mmol) in 2-ethoxyethanol/H2O (20 mL, 3:1) was heated to about 80° C. and stirred for about 18 hours. The resulting dimers 33 were isolated in excess of water and subsequently reacted with 2 equiv of the carbazole-ligand derivative 4 (477 mg, 1.2 mmol) and 5 equiv of Na$_2$CO$_3$ (313 mg, 2.95 mmol) in 2-ethoxyethanol (10 mL) at about 100° C. for about 18 hours. The solvent was removed under reduced pressure, and the compound was purified by column chromatography (silicagel, eluent hexane/dichloromethane 4:1). The product 17 was obtained as yellow solid; 411 mg (43%). TLC Rf=0.30 (hexane/dichloromathene 4:1); $^1$H NMR (CDCl$_3$) δ1.26, 1.29 (s, 9H, isomeric), 1.37, 1.40 (s, 9H, isomeric), 2.67-2.73 (m, 2H), 3.19, 3.28 (t, 2H, J=7.7 Hz, isomeric), 5.63 (s, 1H), 7.00, 7.08 (t, 1H, J=6.6 Hz, isomeric), 7.12-7.20 (m, 1H), 7.22-7.30 (m, 2H), 7.32-7.41 (m, 5H), 7.45-7.51 (m, 4H), 7.52-7.60 (m, 1H), 7.70 (t, 1H, J=8.4 Hz), 7.75-7.81 (m, 1H), 8.13 (d, 2H, J=7.7 Hz), 8.87, 8.97 (d, 1H, J=5.5 Hz, isomeric).

Compounds 18-22

Compounds 18-22 were obtained in a similar manner as Compound 17 from the step (1.10.1) to the step (1.10.2) except, as indicated in Table 2, selected respective boronic acid derivatives were employed to obtain the respective dimer of steps 1.10.1 to 1.10.2. For Compound 18, commercially available 2-(tolyl)pyridine was employed instead of synthesizing a pyridine derivative as in Example 1.10.1.

2.69-2.72 (m, 2H), 3.17-3.25 (m, 2H), 5.61, 5.62 (s, 1H, isomeric), 6.91-6.93 (m, 2H), 7.00, 7.08 (t, 1H, J=6.6 Hz, isomeric), 7.25-7.30 (m, 2H), 7.31-7.44 (m, 5H), 7.50 (s,

TABLE 2

| Compound | Step 1.10.1 | Step 1.10.1 | Boronic acid derivative | Step 1.10.2 |
|---|---|---|---|---|
| Compound 18 | 2-(tolyl)pyridine | [4-methylphenyl-2-pyridine] | | [4-methylphenyl-2-pyridine] |
| Compound 17 | | [4-tert-butylphenyl-2-pyridine] | [4-tert-butylphenyl boronic acid] | |
| Compound 19 | | [4-(trifluoromethyl)phenyl-2-pyridine] | [4-(trifluoromethyl)phenyl boronic acid] | |
| Compound 20 | | [3,5-bis(trifluoromethyl)phenyl-2-pyridine] | [3,5-bis(trifluoromethyl)phenyl boronic acid] | |
| Compound 21 | | [4-methyl-2-fluorophenyl-2-pyridine] | [4-methyl-2-fluorophenyl boronic acid] | |
| Compound 22 | | [4-tert-butyl-2-fluorophenyl-2-pyridine] | [4-tert-butyl-2-fluorophenyl boronic acid] | |

The respective end products were identified as the respective Compound (18-22) as follows.

4H), 7.51-7.60 (m, 1H), 7.70 (t, 1H, J=8.4 Hz), 7.79 (t, 1H, J=7.7 Hz), 8.10-8.14 (m, 2H), 8.88, 8.97 (d, 1H, J=5.5 Hz).

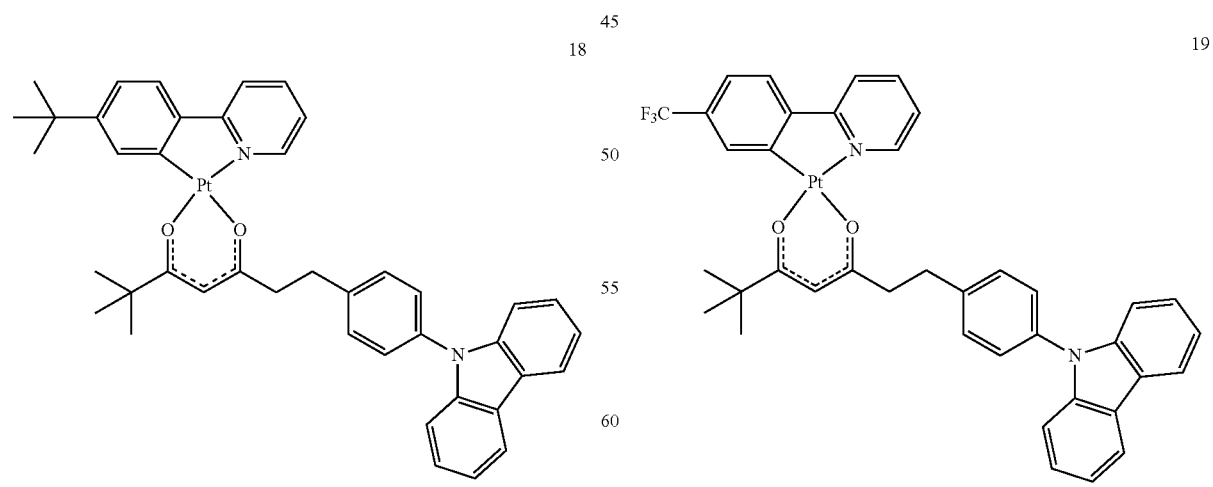

18

19

The product 18 was obtained as yellow solid; 400 mg (44%). TLC Rf=0.30 (hexane/dichloromathene 4:1); $^1$H NMR (CDCl$_3$) δ1.25, 1.27 (s, 9H, isomeric), 2.40 (s, 3H), The product 19 was obtained as yellow solid; 251 mg (yield: 26%). TLC Rf=0.30 (hexane/dichloromathene 4:1); $^1$H NMR (CDCl$_3$) δ1.26, 1.28 (s, 9H, isomeric), 2.70-2.76

(m, 2H), 3.19-3.23 (m, 2H), 5.65, 5.67 (s, 1H, isomeric), 7.12-7.18 (m, 0.5H, isomeric), 7.22-7.30 (m, 2H), 7.32-7.38 (m, 5H), 7.47-7.50 (m, 4H), 7.51-7.60 (m, 1H), 7.64-7.73 (m, 1H), 7.78-7.82 (m, 0.5H, isomeric), 7.88-7.92 (m, 1H), 7.95-7.97 (m, 1H), 8.13 (d, 2H, J=6.6 Hz), 8.94, 9.05 (d, 1H, J=5.5 Hz, isomeric).

20

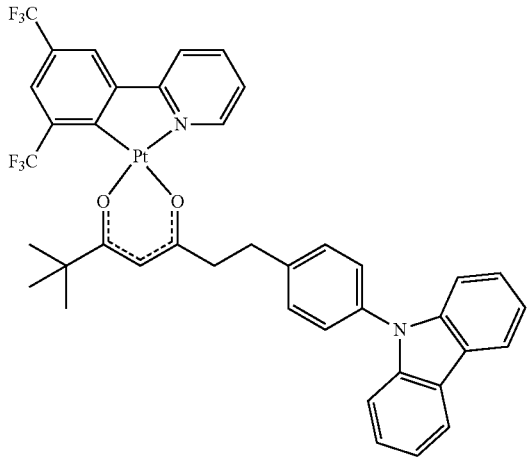

The product 20 was obtained as yellow solid; 110 mg (12%). TLC Rf=0.30 (hexane/dichloromathene 4:1); $^1$H NMR (CDCl$_3$) δ1.24 (s, 9H), 2.73 (t, 2H, J=8.4 Hz), 3.12 (t, 2H, J=8.4 Hz), 5.67 (s, 1H), 7.24-7.32 (m, 3H), 7.37-7.40 (m, 4H), 7.44-7.50 (m, 4H), 7.76 (d, 1H, J=8.1 Hz), 7.85 (d, 1H, J=7.4 Hz), 7.95 (d, 1H, J=7.4 Hz), 8.13 (d, 2H, J=7.7 Hz), 9.20 (d, 1H, J=5.5 Hz).

21

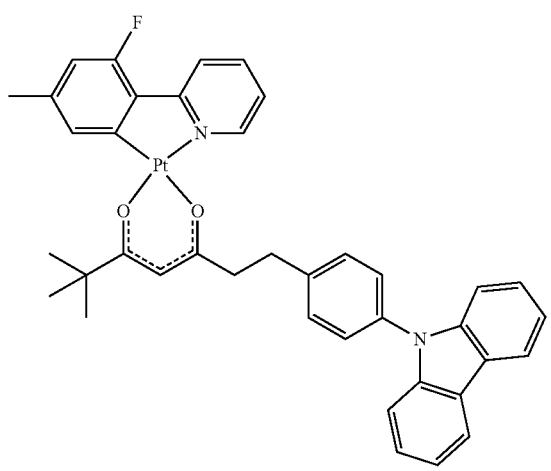

The product 21 was obtained as yellow solid; 620 mg (52%). TLC Rf=0.30 (hexane/dichloromathene 4:1); $^1$H NMR (CDCl$_3$) δ1.25, 1.27 (s, 9H, isomeric), 2.38, 2.39 (s, 3H, isomeric), 2.69-2.74 (m, 2H), 3.18-3.21 (m, 2H), 5.62, 5.64 (s, 1H, isomeric), 6.59-6.65 (m, 1H), 7.03 (t, 1H, J=7.7 Hz), 7.11 (t, 1H, J=7.3 Hz), 7.25-7.28 (m, 3H), 7.32-7.40 (m, 4H), 7.46-7.48 (m, 4H), 7.73, 7.81 (t, 1H, J=6.6 Hz, isomeric), 7.96-8.02 (m, 1H), 8.12 (d, 2H, J=7.7 Hz), 8.93, 9.03 (d, 1H, J=5.5 Hz).

22

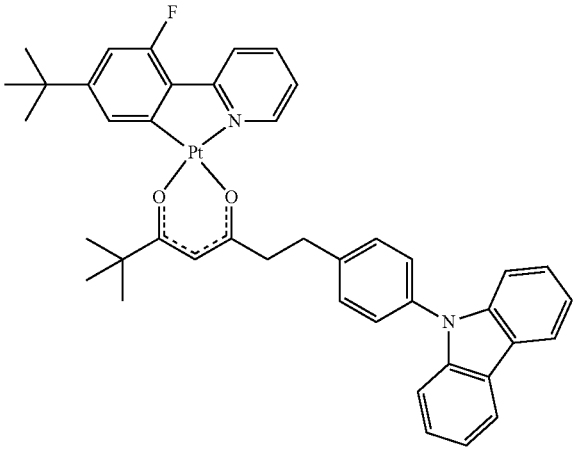

The product 22 was obtained as yellow solid; 387 mg (47%). TLC Rf=0.30 (hexane/dichloromathene 4:1); $^1$H NMR (CDCl$_3$) δ1.25, 1.28 (s, 9H, isomeric), 1.35, 1.38 (s, 9H, isomeric), 2.69-2.74 (m, 2H), 3.19, 3.26 (t, 2H, J=8.0 Hz), 5.63 (s, 1H), 6.80-6.81, 6.85-6.86 (m, 1H, isomeric), 7.03, 7.12 (t, 1H, J=7.3 Hz, isomeric), 7.25-7.30 (m, 2H), 7.31-7.38 (m, 4H), 7.46-7.49 (m, 4H), 7.55, 7.59 (d, 1H, J=1.4 Hz, isomeric), 7.73, 7.82 (t, 1H, J=7.7 Hz, isomeric), 7.96-8.02 (m, 1H), 8.13 (d, 2H, J=7.7 Hz), 8.92, 9.02 (d, 1H, J=5.5 Hz).

Example 2

Device Fabrication

Fabrication of Light-Emitting Device (Using Compound 9 as Example):

Wet process: the ITO-coated glass substrates were cleaned by ultrasound in acetone, and consecutively in 2-propanol, baked at about 110° C. for about 3 hours, then treated with oxygen plasma for 5 min. A layer of PEDOT:PSS (Baytron P purchased from H.C. Starck) was spin-coated at 3000 rpm onto the pre-cleaned and O$_2$-plasma treated (ITO)-substrate and annealed at about 180° C. for about 10 min, yielding a thickness of around 40 nm. Inside a glove-box that hosted a vacuum deposition system at a pressure of about 10$^{-7}$ torr (1 torr=133.322 Pa), a solution of Compound 9 in chlorobenzene was spin-coated on top of the pretreated PEDOT:PSS layer, yielding a 70 nm thick emissive layer. Next a layer of 1,3,5-tris(N-phenylbenzimidizol-2-yl)benzene (TPBI) was deposited on top of the emissive layer at deposition rate of about 0.06 nm/s at a pressure of about 10$^{-7}$ torr (1 torr=133.322 Pa). CsF and Al were then deposited successively at deposition rates of about 0.005 and about 0.2 nm/s, respectively. Each individual device had an area of about 0.14 cm$^2$. All spectra were measured with an Ocean Optics HR 4000 spectrometer and I-V-L characteristics were taken with a Keithley 2400 SourceMeter and Newport 2832-C power meter and 818 UV detector. All device operation was performed inside a nitrogen-filled glove-box.

Dry process: the ITO coated glass substrates were cleaned by ultrasound in acetone, and consecutively in 2-propanol, baked at about 110° C. for about 3 hours, then treated with oxygen plasma for 5 min. A layer of PEDOT: PSS (Baytron P purchased from H.C. Starck) was spin-coated at 3000 rpm onto the pre-cleaned and $O_2$-plasma treated (ITO)-substrate and annealed at about 180° C. for about 10 min, yielding a thickness of about 40 nm. Inside a glove-box hosted vacuum deposition system at a pressure of about $10^{-7}$ torr, 4,4'-bis [N-(naphthyl)-N-phenyl-amino]biphenyl (NPB) was first deposited on top of PEDOT/PSS layer at a deposition rate of about 0.06 nm/s, yielding a 40 nm thick film, followed by deposition of a 20 nm layer of 1,3-N,N-dicarbazole-benzene (mCP). Then Compound 9 was vapor deposited on top of mCP yielding a 25 nm neat layer, followed by deposition of a 30 nm layer of 1,3-bis(N,N'-t-butylphenyl)-1,3,4-oxadiazole (OXD-7) at deposition rate of about 0.06 nm/s. CsF and Al were then deposited successively at deposition rates of about 0.005 and 0.2 rinds, respectively. Each individual device had an area of about 0.14 $cm^2$.

The properties of the devices prepared by these methods are summarized in Table 3.

TABLE 3

Figure 2:
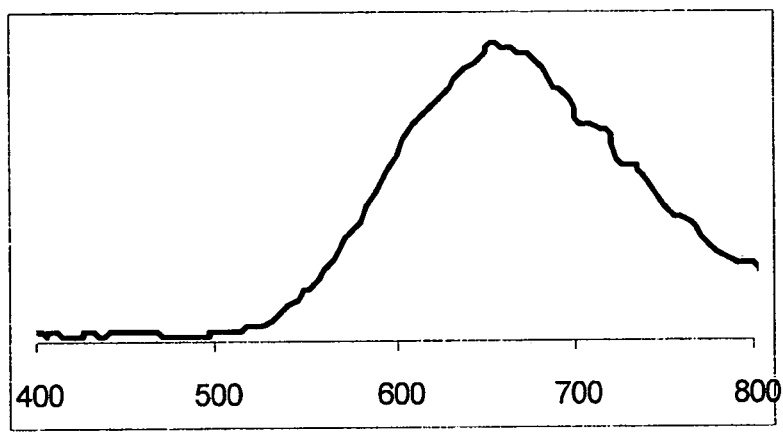
FIG. 2 shows the emission spectrum of a device comprising a control compound.
Figure 3:
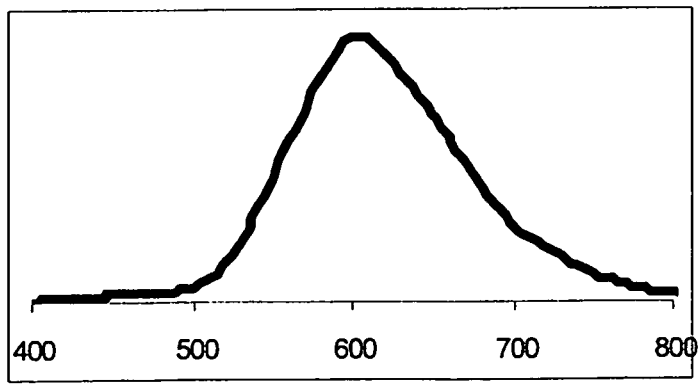
FIG. 3 shows the emission spectrum of an embodiment of a device comprising an embodiment of the compounds disclosed herein.
Figure 4:
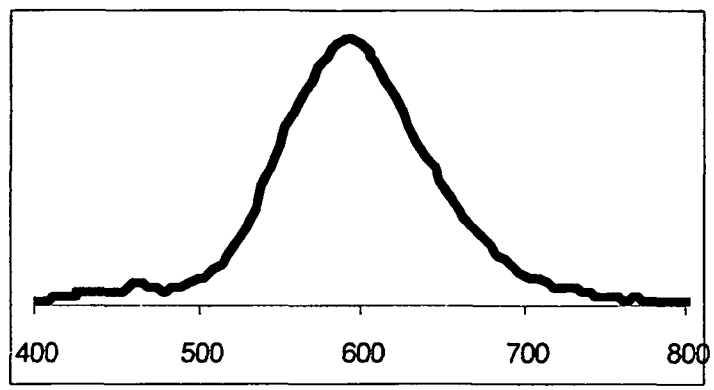
FIG. 4 shows the emission spectrum of an embodiment of a device comprising an embodiment of the compounds disclosed herein.
Figure 5:
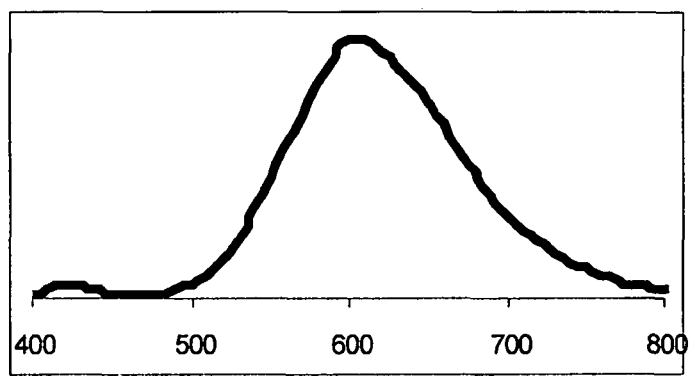
FIG. 5 shows the emission spectrum of an embodiment of a device comprising an embodiment of the compounds disclosed herein.
Figure 6:
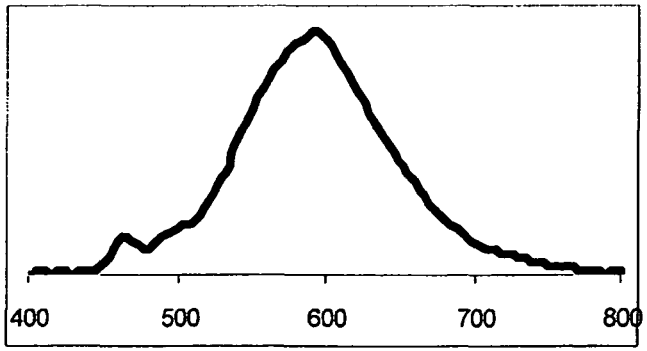
FIG. 6 shows the emission spectrum of an embodiment of a device comprising an embodiment of the compounds disclosed herein.
Figure 7:
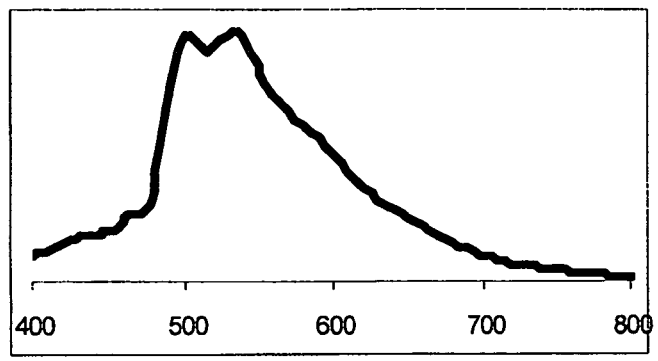
FIG. 7 shows the emission spectrum of an embodiment of a device comprising an embodiment of the compounds disclosed herein.
Figure 8:
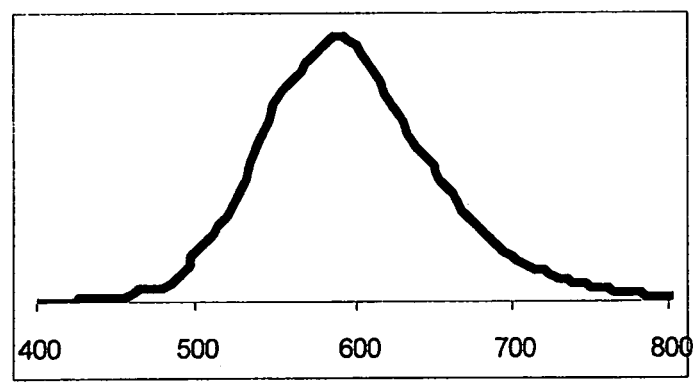
FIG. 8 shows the emission spectrum of an embodiment of a device comprising an embodiment of the compounds disclosed herein.
Figure 9:
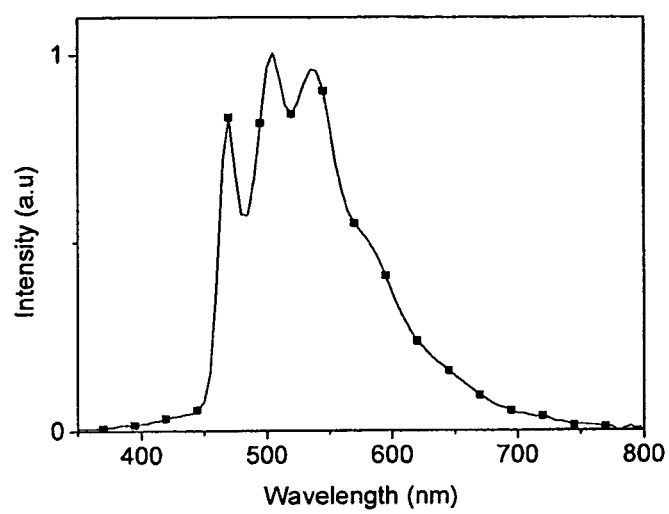
FIG. 9 shows the emission spectrum of an embodiment of a device comprising an embodiment of the compounds disclosed herein.

| Structure | MW | Efficiency (cd/A) | EQE | Spectra | CRI | Td (oC) | Process |
|---|---|---|---|---|---|---|---|
| Comparative Example [FPt] | 484 | 2.0 | 2.6 | FIG. 2 | <60 | 280 | Dry |
| Compound 11 | 740 | 8.4 | 4.4 | FIG. 3 | 64 | 313 | Dry |
| Compound 12 | 782 | 19.7 | 8.2 | FIG. 4 | 60 | 306 | Dry |
| Compound 13 | 796 | 14.7 | 8.1 | FIG. 5 | <60 | 303 | Dry |
| Compound 14 | 1169 | 11.7 | 4.8 | FIG. 6 | 64 | 308 | Wet |
| Compound 15 | 907 | 0.51 | 0.20 | FIG. 7 | <60 | 213 | Dry |
| Compound 16 | 831 | 12.2 | 4.9 | FIG. 8 | <60 | 283 | Dry |
| Compound 9 | 1051 | 14.7 | 5.3 | FIG. 9 | <60 | n/a | Wet |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:
1. A compound represented by Formula VI:

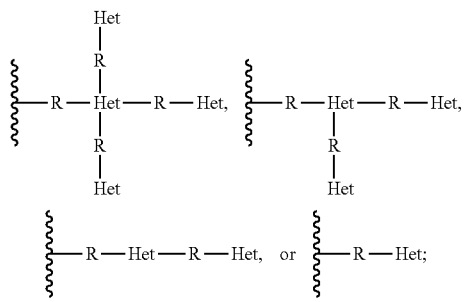

(Formula VI)

wherein, $R^1$, $R^3$, $R^4$, $R^5$, $R^6$, $R^7$, and $R^8$ are independently hydrogen, $C_{1-30}$ alkyl, halo, $C_{1-6}$ haloalkyl, $C_{6-10}$ aryl, or $C_{3-10}$ heteroaryl;

at least one of $R^2$, $R^9$, $R^{10}$ and $R^H$ is independently D;

each D is independently:

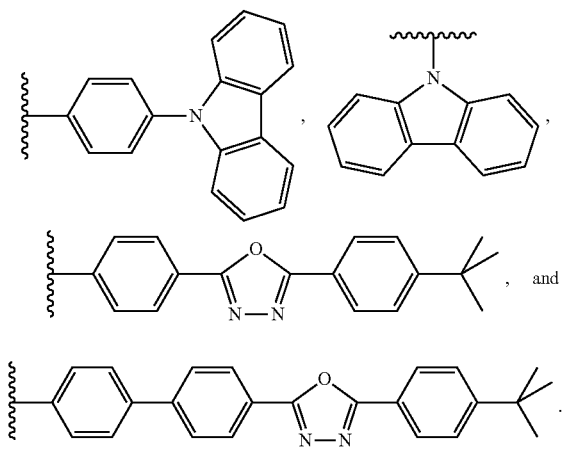

wherein each R is independently $C_{2-4}$ alkylene;

each Het is independently selected from the group consisting of

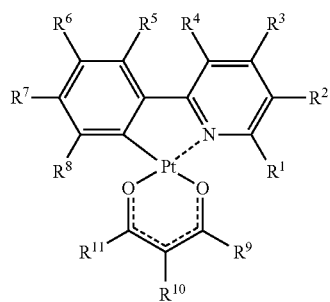

each optionally substituted with alkyl, halogen, alkoxy, or haloalkyl, and any of $R^2$, $R^9$, $R^{10}$ and $R^{11}$ which are not D, are independently hydrogen, $C_{1-30}$ alkyl, $C_{1-30}$ alkoxy, halo, $C_{6-10}$ aryl, or $C_{3-10}$ heteroaryl.

2. The compound of claim 1, wherein at least one of $R^5$, $R^6$, $R^7$, and $R^8$ is halo or $C_{1-6}$ haloalkyl.

3. The compound of claim 2, wherein $R^5$ and $R^7$ are F.

4. The compound of claim 2, wherein $R^6$ and $R^8$ are $CF_3$.

5. The compound of claim 1, wherein each D is independently selected from the group consisting of:

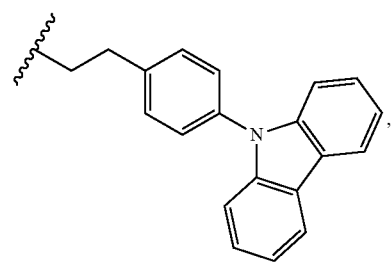 [SMILES: *CCc1ccc(-n2c3ccccc3c3ccccc32)cc1]

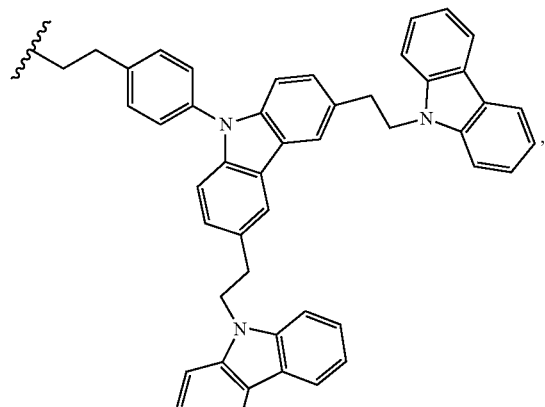
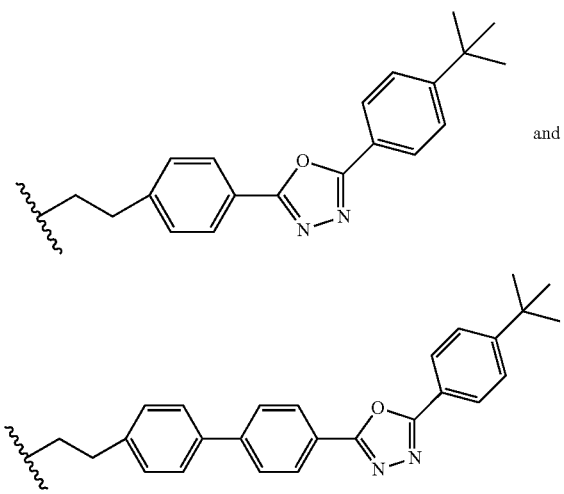
7. The compound of claim 1, wherein R⁹ is:
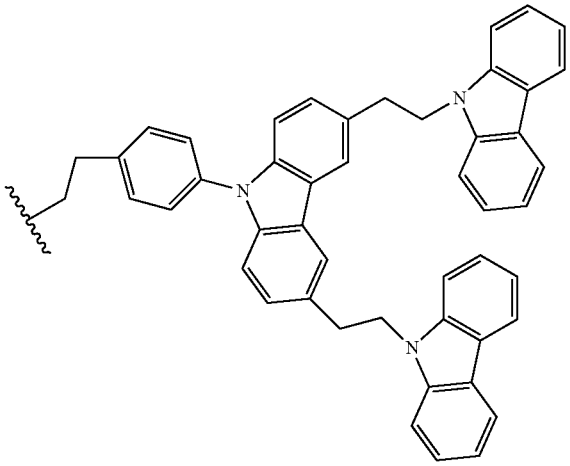
6. The compound of claim 1, wherein R⁹ is:
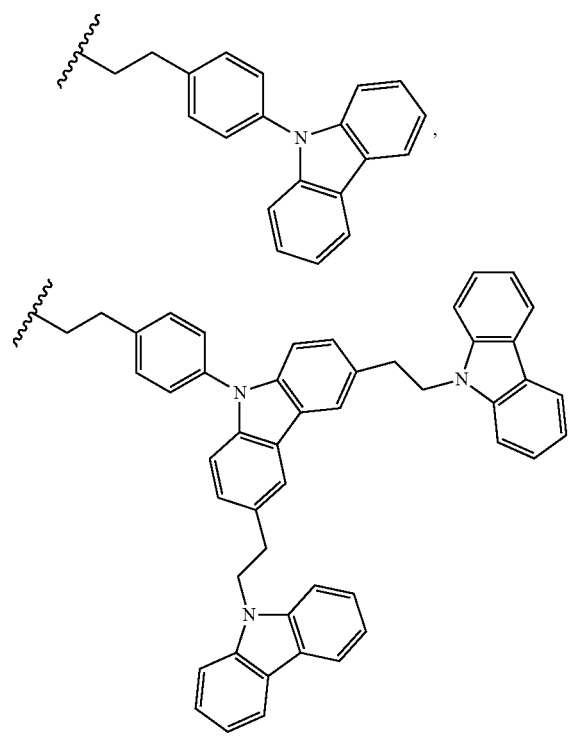
8. The compound of claim 1, wherein at least one of R¹, R², R³, R⁴, R⁵, R⁶, R⁷, R⁸, R⁹, R¹⁰, and R¹¹ is methyl, ethyl, a propyl isomer, a butyl isomer, a pentyl isomer, or a hexyl isomer.
9. The compound of claim 8, wherein R¹¹ is methyl or t-butyl.
10. The compound of claim 1, wherein R² is:
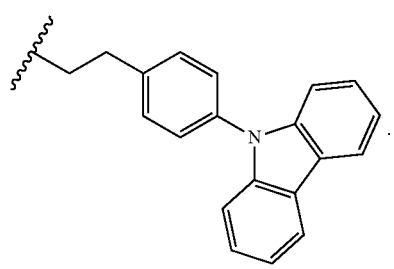

11. The compound of claim 1, wherein R² is:
12. The compound of claim 1, wherein R² is:
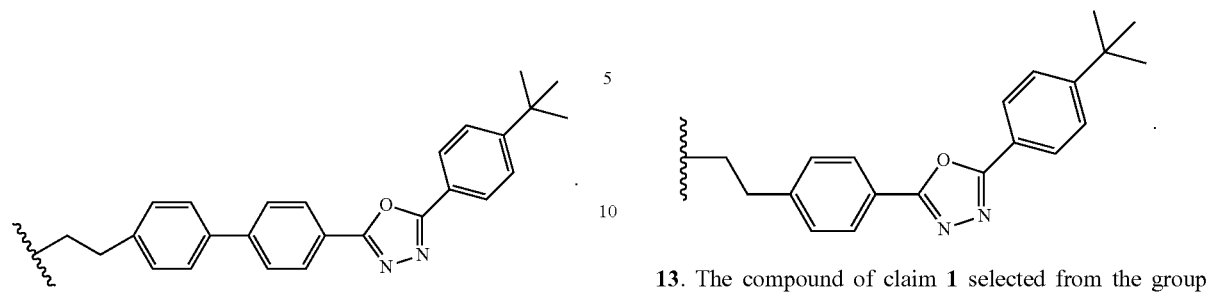
13. The compound of claim 1 selected from the group consisting of:
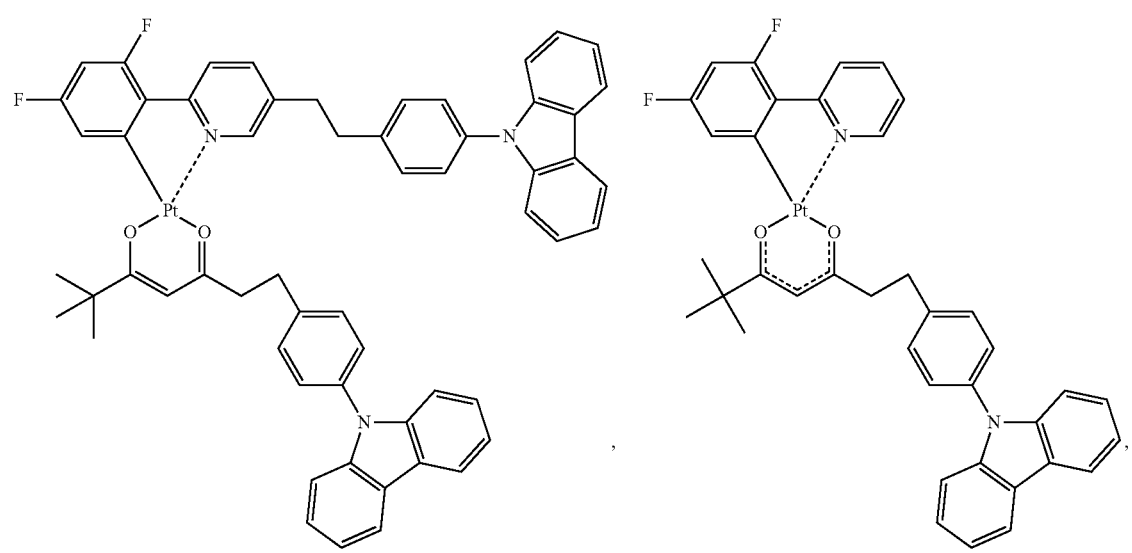
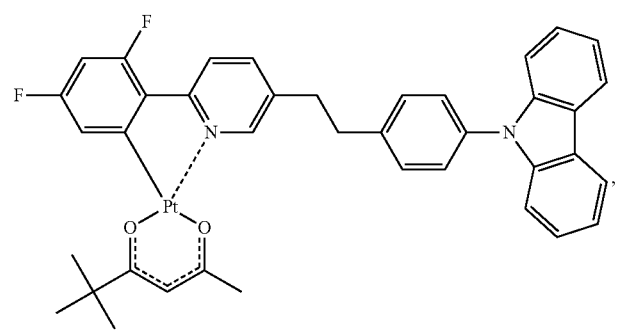
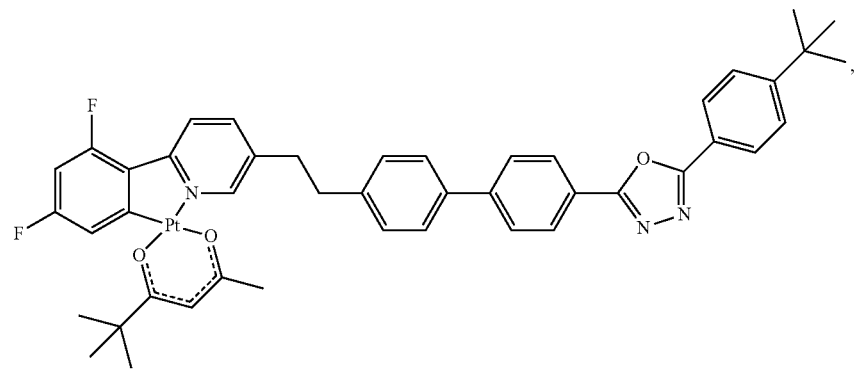

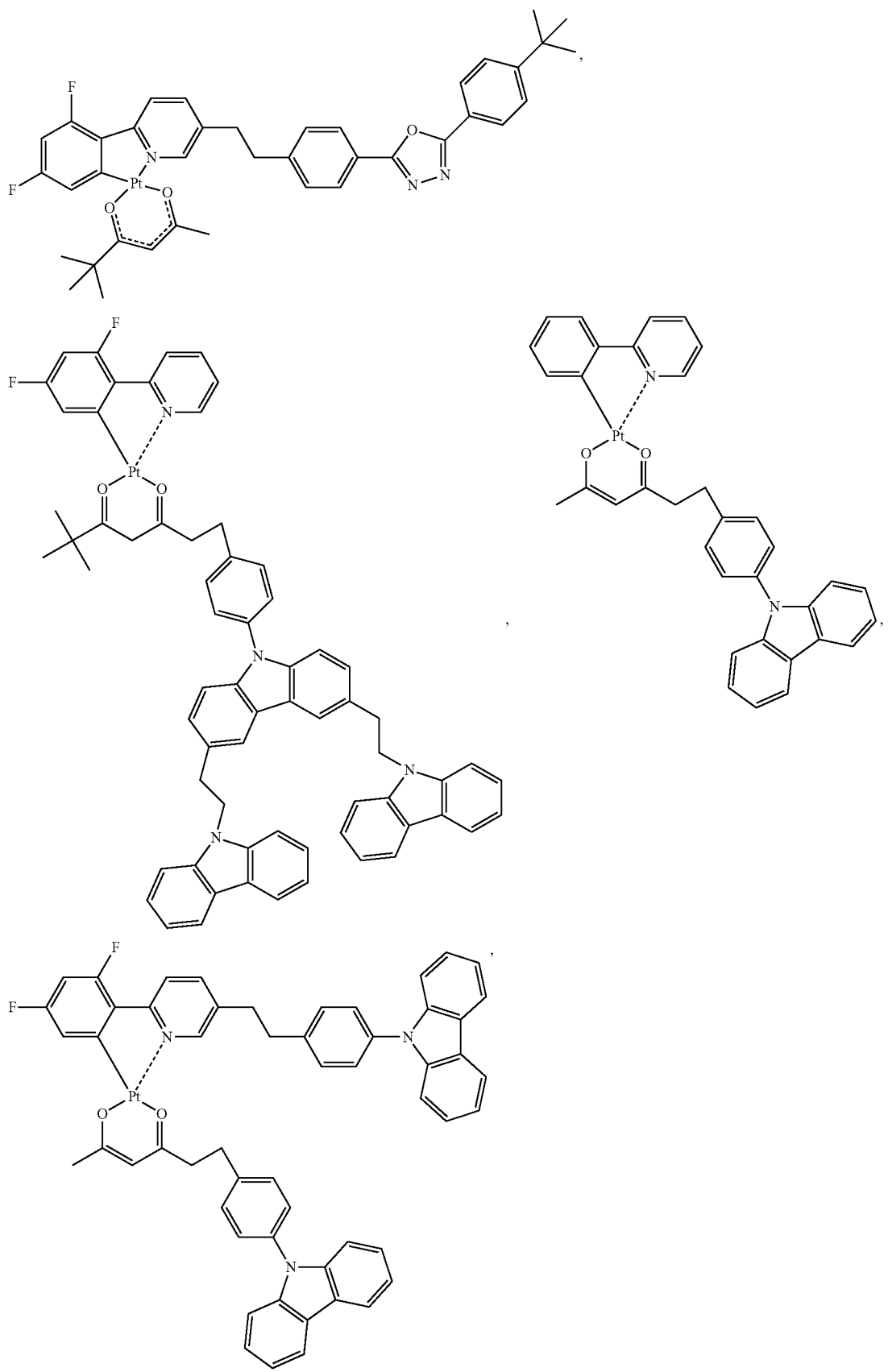

-continued
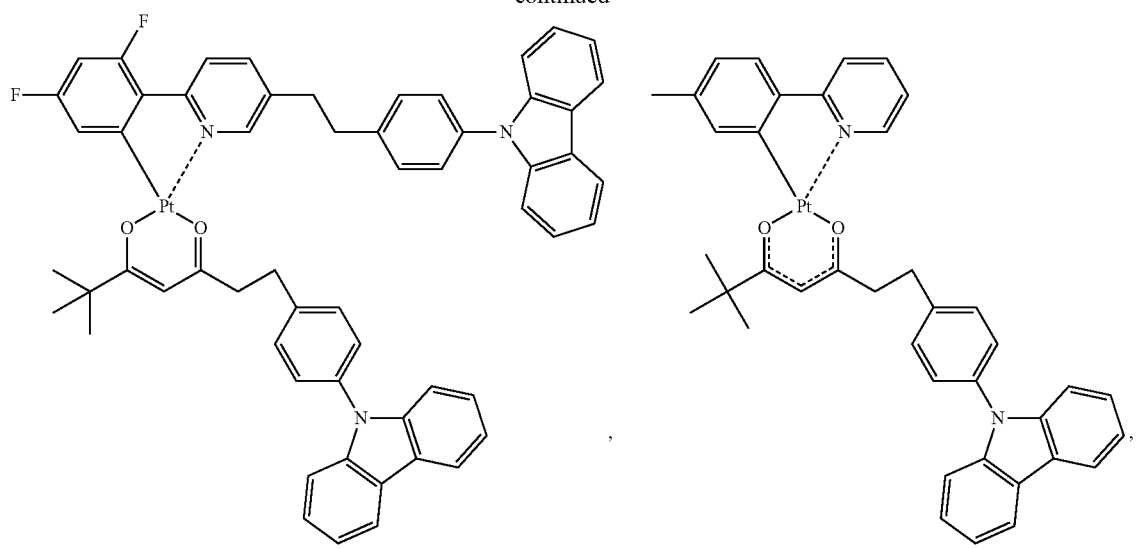
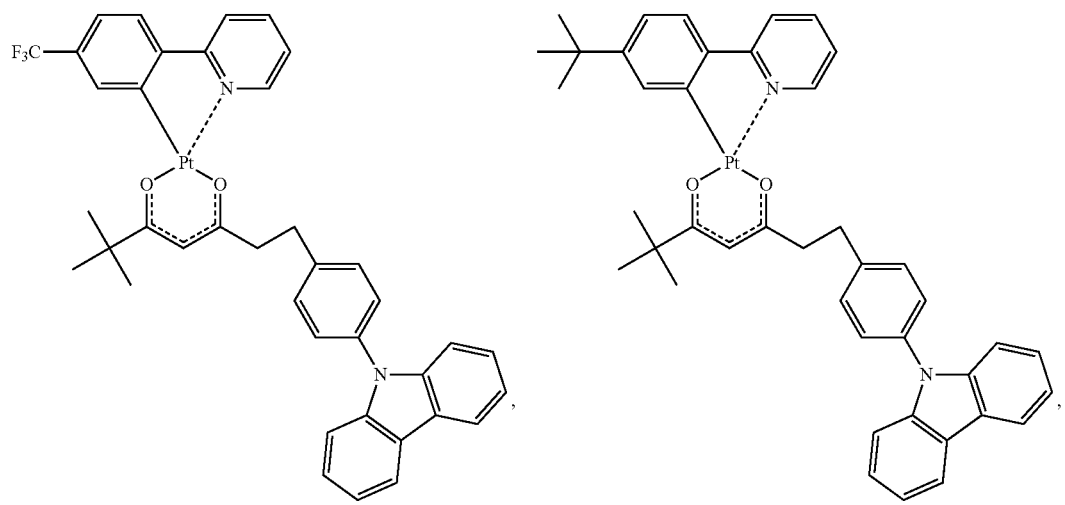
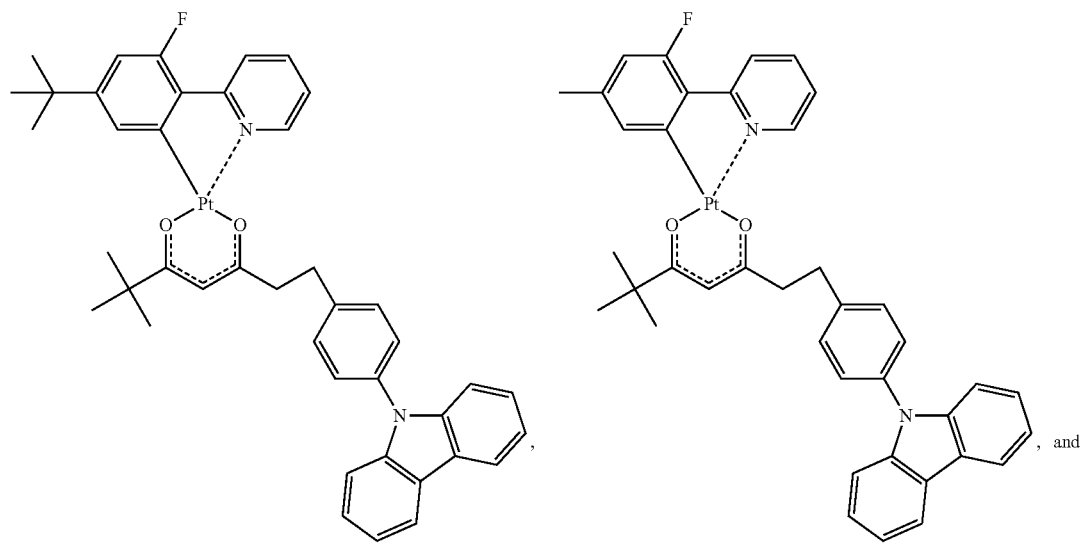

-continued

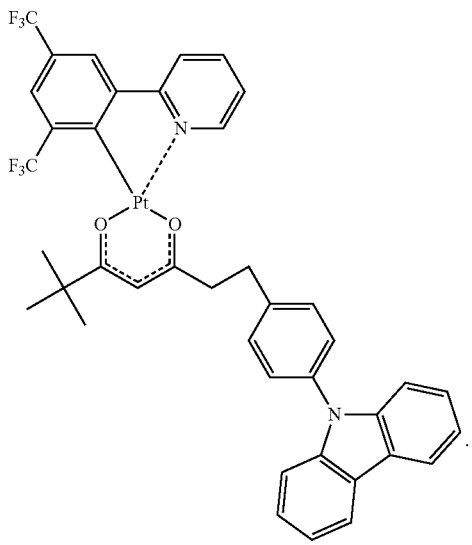

14. A light-emitting device, comprising:
an anode layer;
a cathode layer; and
a light-emitting layer positioned between, and electrically connected to, the anode layer and the cathode layer, wherein the light-emitting layer comprises a compound of claim 1.

15. The device of claim 14, wherein the light-emitting layer comprises the compound without any additional electron-transport or hole-transport material.

16. The device of claim 15, wherein the device comprises no electron-transport or hole-transport layer.

17. The device of claim 16, wherein the device consists essentially of the anode layer, the cathode layer, and the light-emitting layer.

* * * * *